United States Patent
Ishihara et al.

(10) Patent No.: US 6,924,323 B2
(45) Date of Patent: Aug. 2, 2005

(54) SULFONIUM SALT COMPOUND

(75) Inventors: Masami Ishihara, Saitama (JP); Motoshige Sumino, Saitama (JP); Kazuhito Fukasawa, Saitama (JP); Naoki Katano, Saitama (JP); Shigeaki Imazeki, Saitama (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 101 days.

(21) Appl. No.: 10/312,572

(22) PCT Filed: Jun. 27, 2001

(86) PCT No.: PCT/JP01/05512
§ 371 (c)(1),
(2), (4) Date: Jan. 14, 2003

(87) PCT Pub. No.: WO02/18332
PCT Pub. Date: Mar. 7, 2002

(65) Prior Publication Data
US 2004/0033434 A1 Feb. 19, 2004

(30) Foreign Application Priority Data
Aug. 30, 2000 (JP) ......................... 2000-260157

(51) Int. Cl.$^7$ .............................................. G03F 7/004
(52) U.S. Cl. ........................... 522/25; 522/31; 522/57; 522/150; 522/160; 522/113; 430/270.1; 430/281.1; 430/170
(58) Field of Search .......................... 522/25, 31, 148, 522/150–166, 57, 113, 134; 430/269, 270.1, 280.1, 281.1, 170

(56) References Cited

U.S. PATENT DOCUMENTS

| | | | | |
|---|---|---|---|---|
| 5,238,781 A | * | 8/1993 | Schadeli ................... | 430/270.1 |
| 5,369,200 A | * | 11/1994 | Schadeli et al. ............. | 526/262 |
| 5,424,166 A | * | 6/1995 | Pawlowski et al. .......... | 430/157 |
| 5,770,343 A | * | 6/1998 | Sato et al. .................. | 430/170 |
| 5,962,180 A | * | 10/1999 | Iwanaga et al. ............. | 430/170 |
| 6,143,460 A | * | 11/2000 | Kobayashi et al. .......... | 430/170 |
| 6,485,883 B2 | * | 11/2002 | Kodama et al. ............. | 430/170 |
| 6,492,091 B2 | * | 12/2002 | Kodama et al. ........... | 430/270.1 |
| 6,602,646 B1 | * | 8/2003 | Sato et al. ................. | 430/270.1 |
| 6,673,512 B1 | * | 1/2004 | Uenishi et al. ............ | 430/270.1 |
| 6,692,883 B2 | * | 2/2004 | Nishiyama et al. .......... | 430/170 |
| 6,727,036 B2 | * | 4/2004 | Kanna et al. .............. | 430/270.1 |

FOREIGN PATENT DOCUMENTS

| EP | 0 704 762 A1 | 4/1996 |
|---|---|---|
| EP | 1 113 005 A1 | 7/2001 |

OTHER PUBLICATIONS

Derwent WPI—English abstract of JP 51–56885 A, dated May 18, 1976.

* cited by examiner

Primary Examiner—Susan Berman
(74) Attorney, Agent, or Firm—Westerman, Hattori, Daniels and Adrian LLP

(57) ABSTRACT

A compound shown by the general formula [1]

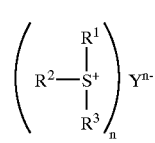

[1]

(wherein $R^1$, $R^2$ and $R^3$ are each independently an aromatic hydrocarbon residual group, $Y^{n-}$ is an anion derived from a carboxylic acid having 3 or more carbon atoms with substituted fluorine atoms, and n is 1 or 2, provided that $R^1$, $R^2$ and $R^3$ each is not a phenyl group having substituents at an ortho and/or a meta position), and a composition consisting of the compound and a diazodisulfone compound are disclosed. Use of the compound or the compound as an acid generator for resists produces the effects of improving the profiles of ultra-fine patterns or diminishing sidewall irregularities in ultra-fine patterns. The compound is also useful as a cationic photopolymerization initiator.

8 Claims, No Drawings

SULFONIUM SALT COMPOUND

TECHNICAL FIELD

The present invention relates to a sulfonium salt compound useful as an acid generator or a photopolymerization initiator.

BACKGROUND ART

In accordance with the recent trend toward higher density integration in semiconductor elements, wavelengths of light sources for irradiation instruments used in fine processing, particularly those for lithography, have become shorter and shorter, and in compliance with this trend, chemically amplified resist compositions have generally been used which utilize an action of an acid generated from an acid generator as a photo-sensitive compound. As an acid generator used in chemically amplified resist compositions, onium salts such as sulfonium salts and iodonium salts, o-nitrobenzylaryl sulfonate compounds, diazodisulfone compounds, disulfone compounds, dicarboxyimide sulfonate compounds, 2-acyloyl-2-aryl sulfonyl propane compounds, triarylsulfonyloxybenzene compounds and the like have been so far examined, and some of them have already been used practically, and even now further studies for improvement have been conducted to meet rules becoming more and more finer.

Sulfonium salts, among others, are one of the major targets for the improvement studies because they are also attracting high attention as a cationic photopolymerization initiator.

Sulfonium salts having $SbF_6^-$, $AsF_6^-$, $PF_6^-$, $BF_4^-$, $CF_3SO_3^-$, or $CF_3COO^-$ as an counter anion, however, have such problems that acids generated are highly volatile, and result in large dimensional deviation and deformation in shape due to the Delay Time caused by a strength of the acids and that an influence of proximity effects is uncontrollable (see, for example, JP-A-5-249682 and JP-A-8-123032). Thus, when sulfonium salts having counter anions mentioned above are used as an acid generator for a chemically amplified resist composition, profiles or side walls of patterns become rough, and therefore, ingredients of a resist forming patterns fall down on a substrate during etching and a pattern itself collapses to make etching unable, and then a quality of semiconductor devices deteriorate.

To solve these problems, a method was proposed to combine an aliphatic diazodisulfone compound generating a weak acid and an onium salt generating a strong acid such as sulfonic acid (see for example JP-A-10-48826), however, the problem of rough pattern profile and side wall has not been solved enough at present.

Therefore, the present invention has been completed under the circumstances as mentioned above and the object of the present invention is to provide a sulfonium salt compound which can be used more practically as an acid generator for a resist and a cationic photopolymerization initiator.

DISCLOSURE OF INVENTION

The present inventors have conducted extensive study in order to attain the above mentioned object to find that a compound shown by the above general formula [1] is an excellent acid generator for a resist or a cationic photopolymerization initiator, and they have accomplished the present invention.

That is, the present invention provides:

(1) A compound shown by the general formula [1]

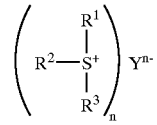

[1]

(wherein $R^1$, $R^2$ and $R^3$ are each independently an aromatic hydrocarbon residual group, $Y^{n-}$ is an anion derived from a carboxylic acid having 3 or more carbon atoms with substituted fluorine atoms, and n is 1 or 2, provided that $R^1$, $R^2$ and $R^3$ each is not a phenyl group having substituents at an ortho and/or a meta position), (2) a composition consisting of the above compound and a diazodisulfone compound, (3) an acid generator comprising the above compound, (4) a resist composition comprising the above compound, and (5) a cationic photopolymerization initiator comprising the above compound.

BEST MODE FOR CARRYING OUT THE INVENTION

In the general formula [1],

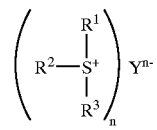

[1]

(wherein $R^1$, $R^2$ and $R^3$ are each independently an aromatic hydrocarbon residual group, $Y^{n-}$ is an anion derived from a carboxylic acid having 3 or more carbon atoms with substituted fluorine atoms, and n is 1 or 2, provided that $R^1$, $R^2$ and $R^3$ is not a phenyl group having substituents at an ortho and/or a meta position), the aromatic hydrocarbon residual groups shown by $R^1$ to $R^3$ include monocyclic and polycyclic types having 6 to 14 carbon atoms, and specifically exemplified by a phenyl group, a naphthyl group, an anthryl group, etc. These aromatic hydrocarbon residual groups may generally have 1 to 10, preferably 1 to 6 substituents. These substituents include $$—R^4 \qquad [2]$$

$$—O—R^5 \qquad [3]$$

$$—S—R^6 \qquad [4]$$

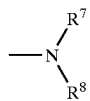

[5]

(wherein, $R^4$, $R^5$ and $R^6$ are each independently a halogen atom, an alkyl group which may have substituents, an aryl group which may have substituents or an aralkyl group which may have substituents, $R^7$ and $R^8$ are each independently a halogen atom, an alkyl group which may have substituents, an aryl group which may have substituents, an aralkyl group which may have substituents or acyl group, $R^7$ and $R^8$ may form a hetero ring together with a nitrogen atom to which they are bound). The compounds with $R^1$ to $R^3$ being phenyl groups having a substituent at o-position and/or m-position are not include in the compounds of the present invention.

In the general formulae [2] to [5], the halogen atom as shown by $R^4$, $R^5$, $R^6$, $R^7$ and $R^8$ is, for example, a chlorine atom, a bromine atom, a fluorine atom, an iodine atom, etc.

The alkyl group of the alkyl group which may have substituents shown by $R^4$, $R^5$, $R^6$, $R^7$ and $R^8$ may be straight chained, branched or cyclic and includes one having generally 1 to 6 carbon atoms, preferably 1 to 4 carbon atoms, which is specifically exemplified by a methyl group, an ethyl group, a propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a 3-methylpentyl group, a 2-methylpentyl group, a 1,2-dimethylbutyl group, a cyclopropyl group, a cyclopentyl group, a cyclohexyl group, etc. The substituents include a halogen atom such as a chlorine atom, a bromine atom, a fluorine atom and an iodine atom, an amino group, a hydroxyl group, etc.

The aryl group of the aryl group which may have substituents shown by $R^4$, $R^5$, $R^6$, $R^7$ and $R^8$ includes a phenyl group, a naphthyl, an anthryl group and a pyrenyl group, and the substituents include an alkyl group having 1 to 4 carbon atoms such as a methyl group, an ethyl group, a propyl group and a butyl group, a halogen atom such as a chlorine atom, a bromine atom, a fluorine atom and an iodine atom, an alkoxy group having 1 to 3 carbon atoms such as a methoxy group, an ethoxy group and a propoxy group, a hydroxyl group, an amino group, a nitro group, etc.

The aralkyl group of the aralkyl group which may have substituents shown by $R^4$, $R^5$, $R^6$, $R^7$ and $R^8$ includes one having generally 7 to 10 carbon atoms, which is specifically exemplified by a benzyl group, a phenethyl group, a phenylpropyl group, etc. The substituents include an alkyl group having 1 to 4 carbon atoms such as a methyl group, an ethyl group, a propyl group and a butyl group, a halogen atom such as a chlorine atom, a bromine atom, a fluorine atom and an iodine atom, an alkoxy group having 1 to 3 carbon atoms such as a methoxy group, an ethoxy group and a propoxy group, a hydroxyl group, an amino group, a nitro group, etc.

The acyl group shown by $R^7$ and $R^8$ includes one derived from aliphatic carboxylic acids having generally 2 to 7 carbon atoms, such as an acetyl group, a propionyl group, a butylyl group, a valeryl group, a hexanoyl group and a heptanoyl group and one derived from aromatic carboxylic acids having generally 7 to 12 carbon atoms, such as a benzoyl group, a toluoyl group, a hydroatropoyl group and a naphthoyl group.

The hetero ring formed by $R^7$, $R^8$ and a nitrogen atom to which they are bound includes 5 to 6 membered rings, which is specifically exemplified by an aromatic hetero ring such as a pyridine ring, a pyrrole ring, a pyrroline ring, a quinoline ring, an indole ring, an isoindoline ring and a carbazole ring, an aliphatic hetero ring such as a pyrrolidine ring and a piperidine ring, etc.

The carboxylic acid which induces anions having 3 or more carbon atoms and fluorine atoms in its molecule shown by $Y^{n-}$ in the general formula [1] includes one shown by the following general formula [6] or [6']:

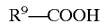   [6]

(wherein, $R^9$ is a monovalent hydrocarbon group having 2 or more carbon atoms and fluorine atoms.)

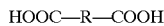   [6']

(wherein, R is a divalent hydrocarbon group having fluorine atoms.)

The hydrocarbon group having 2 or more carbon atoms and fluorine atoms shown by $R^9$ in the general formula [6] includes, for example, an aliphatic hydrocarbon having 2 or more carbon atoms such as an alkyl group and an alkenyl group, an aromatic hydrocarbon group, an aromatic aliphatic hydrocarbon group, etc.

The alkyl group mentioned above may be straight chained, branched or cyclic and includes one having generally 2 or more, preferably 2 to 20, more preferably 2 to 10 carbon atoms, which are specifically exemplified by an ethyl group, an n-propyl group, an isopropyl group, an n-butyl group, an isobutyl group, a sec-butyl group, a tert-butyl group, a n-pentyl group, an isopentyl group, a sec-pentyl group, a tert-pentyl group, a neopentyl group, an n-hexyl group, an isohexyl group, a 3-methylpentyl group, a 2-methylpentyl group, a 1,2-dimethylbutyl group, an n-heptyl group, an isoheptyl gorup, a sec-heptyl group, an n-octyl group, an isooctyl group, a sec-octyl group, an n-nonyl group, an n-decyl group, an n-undecyl group, an n-dodecyl group, an n-tridecyl goup, an n-tetradecyl group, an n-pentadecyl group, an n-hexadecyl group, an n-heptadecyl group, an n-octadecyl group, an n-nonadecyl group, an n-icosyl group, a cyclopropyl group, a cyclopentyl group, a cyclohexyl group, a cycloheptyl group, a cyclooctyl group, a cyclodecyl group, a cyclododecyl group, a cyclotetradecyl group, a cyclohexadecyl group, a cyclooctadexyl group, a cycloicosyl group, etc.

The alkenyl group may be straight chained, branched or cyclic and includes one having generally 2 or more carbon atoms, preferably 2 to 20 carbon atoms, more preferably 2 to 10 carbon atoms, which is specifically exemplified by a vinyl group, an allyl group, a 1-propenyl group, an isopropenyl group, a 3-butenyl group, a 2-butenyl group, a 1-butenyl group, a 1,3-butadienyl group, a 4-pentenyl group, a 3-pentenyl group, a 2-pentenyl group, a 1-pentenyl group, a 1,3-pentadienyl group, 2,4-pentadienyl group, a 1,1-dimethyl-2-propenyl group, a 1-ethyl-2-propenyl group, a 1,2-dimethyl-1-propenyl group, a 1-methyl-1-butenyl group, a 5-hexenyl group, a 4-hexenyl group, a 2-hexenyl group, a 1-hexenyl group, a 1-methyl-1-hexenyl group, a 2-methyl-2-hexenyl group, a 3-methyl-1,3-hexadienyl group, a 1-heptenyl group, a 2-octenyl group, a 3-nonenyl group, a 4-decenyl group, a 1-dodecenyl group, a 1-tetradecenyl group, a 1-hexadecenyl group, a 1-octadecenyl group, a 1-icosenyl group, a 1-cyclopropenyl group, a 2-cyclopentenyl group, a 2,4-cyclopentadienyl group, a 1-cyclohexenyl group, a 2-cyclohexenyl group, a 3-cyclohexenyl group, a 2-cycloheptenyl group, a 2-cyclononenyl group, a 3-cyclodecenyl group, a 2-cyclotridecenyl group, a 1-cyclohexadecenyl group, a 1-cycloctadecenyl group, 1-cycloicosenyl group, etc.

The aromatic hydrocarbon group includes one having generally 6 to 20 carbon atoms, preferably 6 to 14 carbon atoms, which is specifically exemplified by a phenyl group, a naphthyl group, an anthryl group, a 1-pyrenyl group, a perilenyl group, etc.

The aromatic aliphatic hydrocarbon group includes one having generally 7 to 13 carbon atoms, preferably 7 to 10 carbon atoms, which is specifically exemplified by an aralkyl group such as a benzyl group, a phenethyl group, a phenylpropyl group, a phenylbutyl group, a phenylpentyl group, a phenylhexyl group, a phenyl-1-methylhexyl group and a phenyl-3-cyclopentyl group, an arylalkenyl group such as a cinnamyl group and a styryl group, CH=CH—CH$_2$—C$_6$H$_4$—, CH$_2$—CH=CH—C$_6$H$_4$—, etc.

The hydrocarbon group mentioned above may have substituents which is exemplified by an alkyl group having 1 to 4 carbon atoms such as a methyl group, an ethyl group, an n-propyl group, an isopropyl group, an n-butyl group, an isobutyl group, a sec-butyl group and a tert-butyl group, an alkoxy group having 1 to 4 carbon atoms such as a methoxy group, an ethoxy group, a propyloxy group and a butoxy group, etc.

The hydrocarbon group shown by $R^9$ having 2 or more carbon atoms and having fluorine atoms in a molecule is hydrocarbon groups, when it has substituents, in which a part or all of hydrogen atom of the whole hydroxyl group including the substituents are substituted by fluorine atoms.

Thus, an alkyl group and an alkenyl group include one in which a part or all of hydrogen atoms in the whole groups including substituents if any are substituted by fluorine atoms, and above all, the alkyl group and the alkenyl group bounded to carboxylic group, in which all hydrogen atoms bonding to α-position carbon atom are substituted by fluorine atoms, are preferable, and in which all hydrogen atoms bonding to carbon atoms are substituted by fluorine atoms, are more preferable. Further, in groups other than perfluoro types, those groups having a degree of substitution by fluorine atoms are bound to carbon atoms closer to carboxylic groups are more preferable, and which is exemplified by groups in which 1 to 30 hydrogen atoms preferably 1 to 21 hydrogen atoms are substituted by fluorine atoms.

Furthermore, in groups having an alkyl group or an alkoxy group as a substituent, the groups in which only all of hydrogen atom of the substituents are substituted by fluorine atoms, are preferable.

The cyclic alkyl group or the cyclic alkenyl group includes one in which a part or all of hydrogen atoms of the whole groups including the substituents if any are substituted by fluorine atoms. Above all, the groups in which all of hydrogen atoms in the ring are substituted by fluorine atoms are preferable. Further, in the groups having an alkyl group or an alkoxy group as a substituent the groups in which all of only hydrogen atoms of the substituents are preferable The aryl group includes one in which a part or all of hydrogen atoms in the whole groups including the substituents if any are substituted by fluorine atoms. Above all, the groups in which 1 to 5 hydrogen atoms and among others 2 to 3 hydrogen atoms in the aromatic ring are substituted by fluorine atoms are preferable.

The aralkyl group includes one in which a part or all of hydrogen atoms in the whole group including the substituents if any are substituted by fluorine atoms. Above all, the groups in which a part or all of hydrogen atoms in the alkyl moiety and/or 1 to 5 hydrogen atoms in the aromatic ring, and among others, 2 to 3 hydrogen atoms are substituted by fluorine atoms are preferable. Further, in groups having an alkyl group or an alkoxy group as a substituents, the groups all of whose hydrogen atoms are substituted by fluorine atoms are preferable.

The hydrocarbon group having 2 or more carbon atoms and fluorine atoms shown by $R^9$ may have substituents other than the alkyl group and the alkoxy group mentioned above including, for example, halogen atoms such as a chlorine atom, a bromine atom and an iodine atom, an amino group, a nitro group, a carbonyl group, a hydroxyl group, etc.

Specific examples of the compounds shown by the general formula [6] include saturated aliphatic monocarboxylic acids such as 2-fluoropropionic acid, pentafluoropropionic acid, pentafluorobutyric acid, 5H-perfluorovaleric acid, nonafluorovaleric acid, 2,2-bis(trifluoromethyl) propionic acid, perfluorohexanoic acid, 7-chlorododecafluoroheptanoic acid, 7H-perfluoroheptanoic acid, pentadecafluorooctanoic acid, 9H-hexadecafluorononanoic acid, perfluorononanoic acid, 11H-eicosafluorodecanoic acid, nonadecafluorodecanoic acid, perfluorododecanoic acid and perfluorohexadecanoic acid; hydroxy saturated aliphatic monocarboxylic acids such as 2,2-bis(trifluoromethyl)-2-hydroxyacetic acid, 2-hydroxy-2-(trifluoromethyl)butyric acid and 3-hydroxy-2-(trifluoromethyl)propionic acid, unsaturated aliphatic monocarboxylic acids such as 2-(trifluoromethyl)propenoic acid, alicyclic monocarboxylic acids such as perfluorocyclohexyl carboxylic acid and 4-(trifluoromethyl)cyclohexane carboxylic acid, aromatic monocarboxylic acids such as 2-fluorobenzoic acid, 3-fluorobenzoic acid, 4-fluorobenzoic acid, 2,4-difluorobenzoic acid, pentafluorobenzoic acid, 2-bromo-4-fluorobenzoic acid, 4-bromo-2-fluorobenzoic acid, 3-chloro-2,4-difluorobenzoic acid, 3-chloro-2,6-difluorobenzoic acid and 2-chloro-6-fluorobenzoic acid, alkyl aromatic monocarboxylic acids such as 2-trifluoromethylbenzoic acid, 3-trifluoromethylbenzoic acid, 4-trifluoromethylbenzoic acid, 2,4-bis(trifluoromethyl) benzoic acid, 2,6-bis(trifluoromethyl)benzoic acid, 3,5-bis (trifluoromethyl)benzoic acid, 2-chloro-6-fluoro-3-methylbenzoic acid, 2-fluoro-4-(trifluoromethyl)benzoic acid and 2,3,4-trifluoro-6-(trifluoromethyl)benzoic acid, alkoxy aromatic monocarboxylic acids such as 2,5-bis(2,2,2-trifluoroethoxy)benzoic acid and 4-(trifluoromethoxy) benzoic acid, alkenyl aromatic monocarboxylic acids such as 4-allyl-2,3,5,6-tetorafluorobenzoic acid, aralkyl monocarboxylic acids such as 4-fluorophenylacetic acid, 2,4-bis (trifluoromethyl)phenylacetic acid, 3,5-bis(trifluoromethyl) phenylacetic acid, 3-chloro-2,6-difluorophenylacetic acid, 2-chloro-6-fluorophenylacetic acid, 2,4-difluoromandelic acid, 2,4-difluorophenylacetic acid, pentafluorophenylacetic acid, 2-trifluoromethylphenylacetic acid and 2,3,4-trifluorophenylacetic acid, arylalkenyl monocarboxylic acids such as 3-bromo-4-fluorocinnamic acid, 4-bromo-2-fluorocinnamic acid, 5-bromo-2-fluorocinnamic acid, 3-chloro-2,6-difluorocinnamic acid, 2-chloro-6-fluorocinnamic acid, 2,4-difluorocinnamic acid, 2-fluorocinnamic acid, 2,3,4-trifluorocinnamic and 4-trifluoromethylcinnamic acid, etc, and above all, the aliphatic monocarboxylic acids are preferable, more preferable examples are pentadecafluorooctanoate and perfluorododecanoate.

In the general formula [6'], the hydrocarbon group in a divalent hydrocarbon group having fluorine atoms shown by R includes, for example, divalent aliphatic hydrocarbon groups such as an alkylene group and an alkenylene group, divalent aromatic hydrocarbon groups and divalent aromatic aliphatic hydrocarbon groups.

The alkylene group may be straight chained, branched or cyclic and includes one having preferably 1–20 carbon atoms, more preferably 1–10 carbon atoms, which is specifically exemplified by a methylene group, an ethylene group, a trimethylene group, a propylene group, a tetramethylene group, a 1-methyl-trimethylene group, a 2-methyltrimethylene group, a pentamethylene group, a 1-methyltetramethylene group, a 2-methyltetramethylene group, a 1,1-dimethyltrimethylene group, a 1,2-dimethyltrimethylenegroup, a 1,3-dimethyltrimethylene group, a 2-ethyltrimethylene group, a hexamethylene group, a 1-methylpentamethylene gorup, a 2-methylpentamethylene group, a 3-methylpentamethylene group, a 1,2-dimethyltetramethylene group, a 1,3-dimethyltetramethylene group, a 2,3-dimethyltetramethylene group, a 1,1- dimethyltetramethylene group, a 1-ethyltetramethylene group, a 2-ethyltetramethylene group, a 1-ethyl-2-methyltrimethylene group, a heptamethylene group, a 1-methylhexamethylene group, an octamethylene group, a 1-methylheptamethylene group, a nonamethylene group, a 1-methyloctamethylene group, a decamethylene group, a 1-methylnonamethylene group, a dodecamethylene group, a tetradodecamethylene group, an eicosamethylene group, a cyclopropylene group, a cyclopentylene group, a cyclohexylene group, a cycloheptylene group, a cyclooctylene group, a cyclononylene group, a cyclodecylene group, a cyclotetradecylene group, a tetrahexadecylene group, a cycloeicosylene group, an adamantandiyl group, a tricyclo [$5.2.1.0^{2,6}$] decanediyl group, a norbonanediyl group, a methylnorbonanediyl group, an isobornanediyl group, a decalinediyl group, etc.

The alkenylene group may be straight chained, branched or cyclic, and includes one having preferably 2 to 20 carbon atoms, more preferably 2 to 10 carbon atoms, which is specifically exemplified by a vinylene group, a propenylene group, a 1-butenylene group, a 2-butenylene group, a 1,3-butadienylene group, a 1-methylpropenylene group, a 1-methyl-2-propenylene group, a 1-pentenylene group, a 2-pentenylene group, a 1,3-pentadienylene group, a 1,4-pentadienylene group, a 1-methylbutenylene group, a 1-methyl-1,2-butadienylene group, a 1-hexenylene group, a 2-hexenylene group, a 3-hexenylene group, a 1-methylpentenylene group, a 2-methyl-2-pentenylene group, a 1,1-dimethyl-2-propenylene group, a 1-ethyl-2-propenylene group, a 1,2-dimethylpropenylene group, a 1-methyl-1-butenylene, a 1-heptenylene group, a 1-methylhexenylene group, a 2-methyl-2-hexenylene group, a 1,2-dimethylpentenylene group, a 1-octenylene group, a 2-octenylene group, a 3-nonenylene group, a 4-decenylene group, a 1-tridecenylene group, a 1-hexadecenylene group, a 1-octadecenylene group, a 1-eicosenylene group, a 1-cyclopropenylene group, a 2-cyclopentenylene group, a 2,4-cyclopentadienylene group, a 1-cyclohexenylene group, a 2-cyclohexenylene group, a 1-cycloheptenylene group, a 2-cyclononenylene group, a 3-cyclodecenylene group, a 2-cyclododecenylene group, a 1-cyclotetradecenylene group, a 2-cyclopentadecenylene group, a 1-cycloheptadecenylene group, a 2-cyclononadecenylene group, a 4-cycloeicosenylene group, etc.

The divalent aromatic hydrocarbon group includes one having generally 6 to 20 carbon atoms, preferably 6 to 14 carbon atoms, which is specifically exemplified by an o-phenylene group, a m-phenylene group, a p-phenylene group, a diphenylene group, a p-xylene-α, α'-diyl group, etc.

The divalent aromatic aliphatic hydrocarbon group includes one having generally 7 to 13 carbon atoms, preferably 7 to 10 carbon atoms, which is specifically exemplified by —CH$_2$—C$_6$H$_4$—, —CH$_2$—C$_6$H$_4$—CH$_2$—, —CH$_2$—CH$_2$—C$_6$H$_4$—CH$_2$—, —CH(CH$_3$)—CH$_2$—C$_6$H$_4$—, —CH=CH—C$_6$H$_4$—, —CH=CH—CH$_2$—C$_6$H$_4$—, —CH=CH—CH$_2$—C$_6$H$_4$—CH$_2$—, etc.

The divalent hydrocarbon group mentioned above may have substituents including an alkyl group having 1 to 4 carbon atoms such as a methyl group, an ethyl group, an n-propyl group, an isopropyl group, an n-butyl group, an isobutyl group, a sec-butyl group and a tert-butyl group, and an alkoxy group having 1 to 4 carbon atoms such as a methoxy group, an ethoxy group, a propyloxy group and a butoxy group, etc.

The divalent hydrocarbon group having fluorine atoms shown by R is one in which a part or all of hydrogen atoms of the whole divalent hydrocarbon groups including substituents if any are substituted by fluorine atoms.

That is, the alkylene group and the alkenylene group include one in which a part or all of hydrogen atoms in the whole group including substituents if any are substituted by fluorine atoms. Above all, the groups bounded to a carboxylic group in which hydrogen atoms bonding to α-position or α'-position carbon atoms are substituted by fluorine atoms, are preferable, in which all hydrogen atoms bonding to carbon atoms are substituted by fluorine atoms, are more preferable. Further, other than perfluoro types, the groups having a degree of substitution by fluorine atoms closer to perfluoro types and/or having hydrogen atoms bonding to carbon atoms closer to carboxylic group and being substituted by fluorine atoms are preferable, which is specifically exemplified by one in which 1 to 30, preferably 1 to 21 hydrogen atoms are substituted by fluorine atoms. Furthermore, when the groups have an alkyl group or an alkoxy group as a substituent, the groups in which all of hydrogen atoms only in the substituents are substituted by fluorine atoms are preferable.

The cyclic alkylene group or the cyclic alkenylene group include one in which a part or all of hydrogen atoms in the whole group including substituents if any are substituted by fluorine atoms. Above all, the groups in which all hydrogen atoms in the ring are substituted by fluorine atoms are preferable. Further, when the groups have an alkyl group or an alkoxy group as a substituent, the groups in which all of hydrogen atoms only in the substituents are substituted by fluorine atoms are preferable.

The divalent aromatic hydrocarbon group includes one in which a part or all of hydrogen atoms in the whole group including substituents if any are substituted by fluorine atoms. Above all, the groups in which 1 to 4, preferably 2 to 3 hydrogen atoms in the aromatic ring are substituted by fluorine atoms are preferable. Further, when the groups have an alkyl group or an alkoxy group as a substituent, the groups in which all of hydrogen atoms only in the substituents are substituted by fluorine atoms are preferable.

The divalent aromatic aliphatic hydrocarbon group includes one in which a part or all of hydrogen atoms in the whole group including substituents if any are substituted by fluorine atoms. Above all, the groups in which a part or all of hydrogen atoms in the alkyl group moiety and/or 1 to 4, preferably 2 to 3 hydrogen atoms in the aromatic ring are substituted by fluorine atoms are preferable. Further, when the groups have an alkyl group or an alkoxy group as a substituent, the groups in which all of hydrogen atoms only in the substituents are substituted by fluorine atoms are preferable.

The divalent hydrocarbon group having fluorine atoms shown by R may have substituents other than an alkyl group or an alkoxy group including, for example, halogen atoms such as a chlorine atom, a bromine atom and an iodine atom, an amino group, a nitro group, a carbonyl group, a hydroxyl group, etc.

Specific examples of the compound shown by the general formula [6'] include saturated aliphatic dicarboxylic acids such as difluoromalonic acid, 2,2-difluorosuccinic acid, tetrafluorosuccinic acid, hexafluoroglutaric acid, octafluoroadipic acid, dodecafluorosuberic acid, pergluoro-1,9-nonanedicarboxylic acid and perfluoro-1,10-decandicarboxylic acid, unsaturated aliphatic dicarboxylic acids such as 2,2-difluoromaleic acid, 2,2-difluorofumaric acid, 2,2-difluoro-3-pentenediacid and perfluoro-3-hexenediacid, aromatic dicarboxylic acids such as 3-fluorophthalic acid, tetrafluorophthalic acid and tetrafluoroterephthalic acid, alkylaromatic dicarboxylic acids such as 2,2-bis(3-carboxyphenyl) hexafluoropropane and 2,2-bis(4-carboxyphenyl) hexafluoropropane, etc.

Specific examples of the compound shown by the general formula [1] of the present invention include triphenylsulfonium heptafluorobutanoate, triphenylsulfonium pentadecafluorooctanoate, triphenylsulfonium o-trifluoromethylbenzoate, triphenylsulfonium m-trifluoromethylbenzoate, triphenylsulfonium p-trifluoromethylbenzoate, triphenylsulfonium o-fluorobenzoate, triphenylsulfonium m-fluorobenzoate, triphenylsulfonium p-fluorobenzoate, triphenylsulfonium 2,4-difluorobenzoate, triphenylsulfonium 2,3,4,5,6-pentafluorobenzoate, triphenylsulfonium 4-fluorophenylacetate, triphenylsulfonium perfluorododecanoate, (4-methylphenyl)diphenylsulfonium pentadecafluorooctanoate, di(4-methylpheny) phenylsulfonium pentadecafluorooctanoate, tri(4-methylphenyl)sulfonium pentadecafluorooctanoate, bis(triphenylsulfonium) tetrafluorosuccinate, bis(triphenylsulfonium) dodecafluorosuberinate, bis(triphenylsulfonium) tetrafluorophthalate, etc., and above all, triphenylsulfonium pentadecafluorooctanoate, triphenylsulfonium perfluorododecanoate, etc. are preferable.

The compound shown by the general formula [1] of the present invention can be synthesized, for example, by methods [A], [B] and [C] shown by the following schemes.

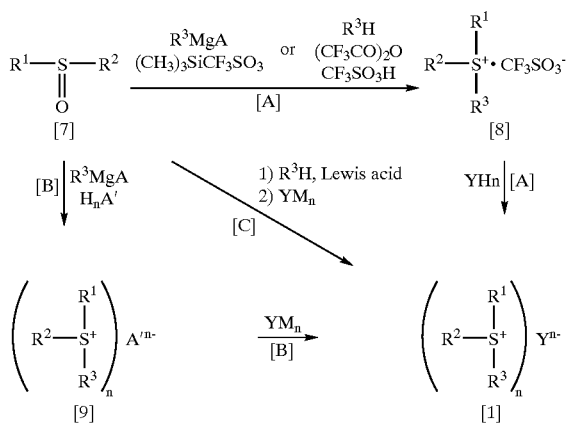

(wherein, A and A' are each independently a halogen atom, M is a metal atom, $R^1$, $R^2$, $R^3$, Y and n are the same as the above.)

The halogen atom shown by A and A' includes, for example, a chlorine atom, a fluorine atom, a bromine atom, an iodine atom, etc.

The metal atom shown by M includes, for example, a silver atom, a lithium atom, a sodium atom, a potassium atom, a rubidium atom, a cesium atom, etc.

The Lewis acid includes, for example, $AlCl_3$, $AlBr_3$, $FeCl_3$, $ZnCl_2$, $SnCl_2$, $BF_3$, $Yb(OTf)_3$, $Sc(OTf)_3$, etc.

That is, in the method [A], a compound shown by the general formula [7] is dissolved in an ether such as ethyl ether, isopropyl ether, tetrahydrofuran and 1,2-dimethoxyethane, a hydrocarbon such as hexane and heptane, an aromatic hydrocarbon such as benzene, or in a mixture of these solvents with a halogenated hydrocarbon solvent such as methylene chloride, methylene bromide, 1,2-dichloroethane and chloroform, followed by an addition of either trimethylsilyl trifluoromethanesulfonate in a molar ratio of 0.8 to 2 and a Grignard reagent ($R^3MgA$) in a molar ratio of 0.5 to 3 to the compound shown by the general formula [7] at −70 to −50° C., or benzene or its derivatives ($R^3H$) in a molar ratio of 1 to 10, trifluoroacetic acid anhydride in a molar ratio of 1 to 3 and trifluoromethanesulfonic acid in a molar ratio of 1 to 3 at 0 to 30° C., and then, the solution is reacted at 0 to 30° C. for 0.5 to 10 hours with stirring to give a compound shown by the general formula [8]. When benzene or its derivative is used, they may be used also as a solvent. And next, the resulting compound shown by the general formula [8] is dissolved in an aqueous solution of alcohol such as methanol, ethanol and isopropanol, and then treated with an anion-exchange resin, followed by an addition of 0.9 to 1.5 mole of an organic carboxylic acid (YH), and distilled the alcohol off, the mixture is again dissolved in an organic solvent such as methylene chloride, 1,2-dichloroethane, ethyl acetate, butyl acetate, propyleneglycol monomethyl ether acetate, methylisobutyl ketone and methylethyl ketone, and then washed with water, followed by concentration under reduced pressure to give a compound of the present invention shown by the general formula [1].

In the method [B], a compound shown by the general formula [7] is dissolved in an ether such as ethyl ether, isopropyl ether, tetrahydrofuran and 1,2-dimethylethane or in a mixture of these solvents with a halogenated hydrocarbon solvent such as methylene chloride, methylene bromide, 1,2-dichloroethane and chloroform or an aromatic hydrocarbon solvent such as benzene, toluene and xylene, followed by an addition of a Grignard reagent ($R^3MgA$) in a molar ratio of 0.5 to 3 to the compound shown by the general formula [7] at −10 to 100° C., if necessary in the presence of a catalyst such as trimethylsilyl triflate and chloromethylsilane, and then reacted at 0 to 100° C. for 0.5 to 10 hours with stirring. After completion of the reaction, the reaction solution is treated with an aqueous solution of hydrogen halide (HA') such as an aqueous solution of hydrogen bromide, an aqueous solution of hydrogen chloride and an aqueous solution of hydrogen iodide at 0 to 30° C., to give a compound shown by the general formula [9]. The resulting compound is then dissolved in, for example, methylene chloride, methanol, ethanol, isopropanol, water or a mixture thereof, followed by an addition of 0.9 to 1.5 mole of a salt of an organic carboxylic acid (YM), and reacted at 0 to 50° C. for 0.5 to 20 hours with stirring to give a compound of the present invention shown by the general formula [1].

In the method [C], a compound shown by the general formula [7] is reacted with benzene or its derivative ($R^3H$) in a molar ratio of 1 to 50 and Lewis acid in a molar ratio of 1 to 10 to said compound at −20 to 180° C. for 0.5 to 24 hours with stirring. The resulting compound is reacted with a salt of an organic carboxylic acid (YM) in a molar ratio of 1 to 5 to the resulting compound at −20 to 100° C. for 0.5 to 24 hours with stirring, to give a compound of the present invention shown by the general formula[1].

The sulfonium salt of the present invention is useful as an acid generator composing a chemically amplified resist composition used in a production of semiconductor elements and can also be exhibited excellent effects as a cationic photopolymerization initiator.

<1> First, use of the sulfonium salt of the present invention as an acid generator for a chemically amplified resist composition will be explained below.

The sulfonium salt of the present invention can be used alone as an acid generator, however, more enhanced effects can be expected when used in combination with other acid generators. Specifically, the sulfonium salt of the present invention, when used in combination with an acid generator generating a weak acid such as a diazodisulfone compound having pending alkyl groups, provides remarkably excellent effects as an acid generator.

The diazodisulfone compound to be used in combination includes, for example, one shown by the general formula [10]:

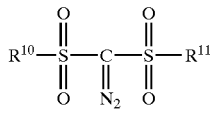

(wherein, $R^{10}$ and $R^{11}$ are each independently an alkyl group.)

The alkyl group shown by $R^{10}$ in the general formula [10] may be straight chained, branched or cyclic and includes one having generally 1 to 8 carbon atoms, which is specifically exemplified by a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a 3-methylpentyl group, a 2-methylpentyl group, a 1,2-dimethylbutyl group, an n-heptyl group, an isoheptyl group, a sec-heptyl group, an n-octyl group, an isooctyl group, a sec-octyl group, a cyclopropyl group, a cyclopentyl group, a cyclohexyl group, a cycloheptyl group, a cyclooctyl group, etc.

The alkyl group shown by $R^{11}$ is preferably branched or cyclic and includes one having generally 3 to 8 carbon atoms, which is specifically exemplified by an isopropyl group, an isobutyl group, a sec-butyl group, a tert-butyl group, an isopentyl group, a sec-pentyl group, a tert-pentyl group, a neopentyl group, an isohexyl group, a 3-methylpentyl group, a 2-methylpentyl group, a 1,2-dimethylbutyl group, an isoheptyl group, a sec-heptyl group, an isooctyl group, a sec-octyl group, a cyclopropyl group, a cyclopentyl group, a cyclohexyl group, a cycloheptyl group, a cyclooctyl group, etc.

Specific examples of the diazodisulfone compound shown by the general formula [10] includes, for example, bis(ethylsulfonyl) diazomethane, bis(1-methylethylsulfonyl) diazomethane, bis(1,1-dimethyethylsulfonyl)diazomethane, bis(cyclohexylsulfonyl)diazomethane, methylsulfonyl-1-methylethylsulfonyldiazomethane, methylsulfonyl-1,1-dimethylethylsulfonyl diazomethane, methylsulfonylcyclohexylsulfonyldiazomethane, ethylsulfonyl-1-methylethylsulfonyldiazomethane, ethylsulfonyl-1,1-dimethylethylsulfonyl diazomethane, ethylsulfonylcyclohexylsulfonyldiazomethane, bis(octanesulfonyl) diazomethane, methylethlsulfonyl-1,1-dimethylethylsulfonyldiazomethane, 1-methylethylsulfonylcyclohexylsulfonyldiazomethane and 1,1-dimethylethyl sulfonylcyclohexylsulfonyldiazomethane. Above all, for example, bis(1-methylethylsulfonyl)diazomethan, bis(1,1-dimethylethylsulfonyl)diazomethan, bis(cyclohexylsulfonyl)diazomethan are preferable, bis(1,1-dimethylethylsulfonyl)diazomethan, bis(cyclohexylsulfonyl)diazomethan are more preferable, and when these compound are used in combination with a sulfonium salt of the present invention, excellent effects can be expected in view of prevention of generation of fine particles and various resist performances.

That is, the acid generator consisting of the combination of triphenylsulfonium pentadecafluorooctanoate with bis(1,1-dimethylethylsulfonyl)diazomethan, triphenylsulfonium pentadecafluorooctanoate with bis(cyclohexylsulfonyl)diazomethan, triphenylsulfonium perfluorododecanoate with bis(1,1-dimethylethylsulfonyl)diazomethan or triphenylsulfonium perfluorododecanoate with bis(cyclohexylsulfonyl) is exhibited excellent efects specifically as a chemically amplified resist.

The amount of the sulfonium salt of the present invention to be used in a single use is generally 0.1 to 10 wt %, preferably 0.5 to 5 wt % relative to a resin amount in a chemically amplified resist composition, and in a case of combined use with other acid generators, it is generally 0.05 to 5 wt %, preferably 0.1 to 3 wt % relative to on a resin amount. The amount of other acid generators to be used is generally 1 to 10 wt %, preferably 3 to 7 wt % relative to a resin amount.

The sulfonium salt of the present invention generates an acid by irradiation with not only deep ultra violet ray and KrF excimer laser but also with i-line, ArF excimer laser, $F_2$ laser (157 nm), electron beam or soft X-ray.

The chemically amplified resists in which the sulfonium salt of the present invention is used are classified into positive type and negative type and the positive type resist is roughly divided into 2 components resist and 3 components resist.

The positive type 2 components resist consists of one or more kinds of polymers (or resins) with pending protecting groups to become soluble in an alkaline developing solution by an action of an acid, one or more kinds of sulfonium salts of the present invention, one or more kinds of acid generators shown by the general formula [10] mentioned above, and optionally used basic compound, acidic compound, ultra violet ray absorber, surfactant and solvent dissolving these compounds.

The positive type 3 components resist consists of one or more kinds of polymers (or resins) which is soluble in an alkaline developing solution, one or more kinds of dissolving-inhibitors with pending protecting groups to become soluble in an alkaline developing solution by an action of an acid, one or more kinds of sulfonium salts of the present invention, one or more kinds of acid generators shown by the general formula [10] and optionally used basic compound, acidic compound, ultra violet ray absorber, surfactant and solvent dissolving these compounds.

The negative type resist consists of one or more kinds of polymers (or resins) which is soluble in an alkaline developing solution, a cross-linking agent to cross-link the polymers by a heat treatment in the presence of an acid to make insoluble in an alkaline developing solution, one or more kinds of sulfonium salts of the present invention, one or more kinds of acid generators shown by the general formula [10] and optionally used basic compound, acidic compound, ultra violet ray absorber, surfactant and solvent dissolving these compounds.

The polymer (or a resin) with pending protecting groups to become soluble in an alkaline developing solution by an action of an acid includes one shown by the following general formula [11]:

[11]

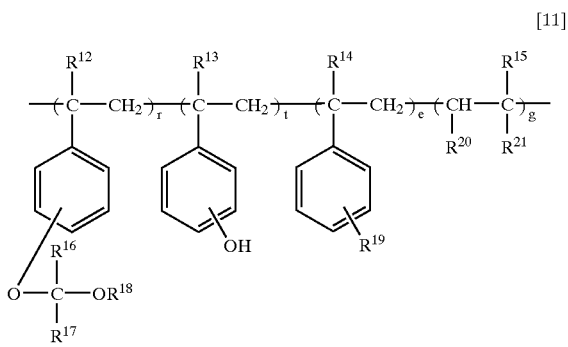

(wherein, $R^{12}$, $R^{13}$, $R^{14}$ and $R^{15}$ are each independently a hydrogen atom or a methyl group, $R^{16}$ is a hydrogen atom or an alkyl group, $R^{17}$ is an alkyl group and $R^{16}$ and $R^{17}$ may form aliphatic ring together with a carbon atom to which they are bound, $R^{18}$ is an alkyl group or an aralkyl group; $R^{19}$ is a hydrogen atom, an alkyl group, an alkoxy group, a tetrahydropyranyloxy group, a tetrahydrofuranyloxy group, a tert-butoxycarbonyloxy group, a tert-amyloxycarbonyloxy group, a benzoyloxy group, an acetyloxy group, a pivaloyloxy group or a tert-butoxycarbonylmethyloxy group, $R^{20}$ is a hydrogen atom or a cyano group, $R^{21}$ is a cyano group or a carboxyl group which may have substituents, t, e and g are 0 or a natural number and r is a natural number, providing that $0 \leq r/r+t+e+g \leq 0.5$, $0 \leq e/r+t+e+g \leq 0.3$, $0 \leq g/r+t+e+g \leq 0.3$, and $0.2 < r+e+g/r+t+e+g \leq 0.8$).

The alkyl group shown by $R^{16}$, $R^{17}$ and $R^{19}$ in the general formula [11] may be straight chained, branched or cyclic and includes one having generally 1 to 6 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a sec-pentyl group, a tert-pentyl group, a neopentyl group, a n-hexyl group, an isohexyl group, a sec-hexyl group, a tert-hexyl group, a 1-methylpentyl group, a 2-methylpentyl group, a 3-methylpentyl group, a cyclopropyl group, a cyclopentyl group, a cyclohexyl group, etc.

The alkyl group shown by $R^{18}$ may be straight chained, branched or cyclic and includes one having generally 1 to 10 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a sec-pentyl group, a tert-pentyl group, a neopentyl group, an n-hexyl group, an isohexyl group, a sec-hexyl group, a tert-hexyl group, a 1-methylpentyl group, a 2-methylpentyl group, a 3-methylpentyl group, an n-heptyl group, an isoheptyl group, a sec-heptyl group, a tert-heptyl group, a 1-methylheptyl group, a 2-methylheptyl group, a 3-methylheptyl group, a 4-methylheptyl group, an n-octyl group, an isooctyl group, a tert-octyl group, an n-nonyl group, an isononyl group, a sec-nonyl group, an n-decyl group, an isodecyl group, a tert-decyl group, a cyclopropyl group, a cyclopentyl group, a cyclohexyl group, a cycloheptyl group, a cyclooctyl group, a cyclononyl group, a cyclodecyl group, etc.

The aralkyl group shown by $R^{18}$ is one having generally 7 to 10 carbon atoms, which is specifically exemplified by a benzyl group, a phenethyl group, a phenylpropyl group, etc.

The alkoxy group shown by $R^{19}$ may be straight chained, branched or cyclic and includes one having generally 1 to 6 carbon atoms, which is specifically exemplified by a methoxy group, an ethoxy group, an n-propoxy group, an isopropoxy group, a cyclopropoxy group, an n-butoxy group, an isobutoxy group, a tert-butoxy group, a sec-butoxy group, an n-pentyloxy group, an isopentyloxy group, a cyclopentyloxy group, an n-hexyloxy group, an isohexyloxy group, a cyclohexyloxy group, a 1-methylpentyloxy group, a 1-methylhexyloxy group, etc.

The substituent of a carboxylic acid which may have substituents shown by $R^{21}$ includes an alkyl group, a bridged alicyclic hydrocarbon group and a mevalonolactone group.

The alkyl group may be straight chained, branched or cyclic and includes one having generally 1 to 8 carbon atoms, which is specifically exemplified by a methyl group, an ethyl group, an n-propyl group, an isopropyl group, a cyclopropyl group, an n-butyl group, an isobutyl group, a tert-butyl group, a sec-butyl group, an n-pentyl group, an isopentyl group, a sec-pentyl group, a tert-pentyl group, a neopentyl group, a cyclopentyl group, an n-hexyl group, an isohexyl group, a sec-hexyl group, a tert-hexyl group, a 1-methylpentyl group, a cyclohexyl group, an n-heptyl group, an isoheptyl group, a sec-heptyl group, a tert-heptyl group, a cycloheptyl group, an n-octyl group, an isooctyl group, a sec-octyl group, a tert-octyl group, a cyclooctyl group, etc.

The bridged alicyclic hydrocarbon group is one having generally 7 to 12 carbon atoms and includes, for example, an isobornyl group, a norbornyl group, a 2-adamanthyl group, a 2-methyl-2-adamanthyl group, etc.

Specific examples of the polymer shown by the general formula [11] include poly(p-1-ethoxyethoxystyrene/p-hydroxystyrene), poly(p-1-ethoxyethoxystyrene/p-hydroxystyrene/p-tert-butoxystyrene), poly(p-1-ethoxyethoxystyrene/p-hydroxystyrene/p-tert-butoxycarbonyloxystyrene), poly(p-1-ethoxyethoxystyrene/p-hydroxystyrene/p-tetrahydropyranyloxystyrene), poly(p-1-ethoxyethoxystyrene/p-hydroxystyrene/p-tert-butoxycarbonylmethyloxystyrene), poly(p-1-ethoxyethoxystyrene/p-hydroxystyrene/p-isopropoxystyrene), poly(p-1-ethoxyethoxystyrene/p-hydroxystyrene/p-benzoyloxystyrene), poly(p-1-ethoxyethoxystyrene/p-hydroxystyrene/p-pivaloyloxystyrene), poly(p-1-ethoxyethoxystyrene/p-hydroxystyrene/tert-butylacrylate), poly(p-1-ethoxyethoxystyrene/p-hydroxystyrene/2-adamanthylacrylate), poly(p-1-ethoxyethoxystyrene/p-hydroxystyrene/isobornylacrylate), poly(p-1-ethoxyethoxystyrene/p-hydroxystyrene/cyclohexylacrylate), poly(p-1-ethoxyethoxystyrene/p-hydroxystyrene/methylmethacrylate), poly(p-1-ethoxyethoxystyrene/p-hydroxystyrene/styrene/tert-butylacrylate), poly(p-1-ethoxyethoxystyrene/p-hydroxystyrene/styrene/tert-amylacrylate), poly(p-1-ethoxyethoxystyrene/p-hydroxystyrene/styrene/1-methylcyclohexylacrylate), poly(p-1-ethoxyethoxystyrene/p-hydroxystyrene/styrene/mevalonolactoneacrylate), poly(p-1-ethoxypropoxystyrene/p-hydroxystyrene), poly(p-1-ethoxypropoxystyrene/p-hydroxystyrene/p-tert-butoxystyrene), poly(p-1-ethoxypropoxystyrene/p-hydroxystyrene/p-tert-butoxycarbonyloxystyrene), poly(p-1-ethoxypropoxystyrene/p-hydroxystyrene/p-tetrahydropyranyloxystyrene), poly(p-1-isobutoxyethoxystyrene/p-hydroxystyrene), poly(p-1-cyclohexyloxyethoxystyrene/p-hydroxystyrene), poly(p-1-cyclohexyloxyethoxystyrene/p-hydroxystyrene/p-tert-butoxystyrene), poly(p-1-cyclohexyloxyethoxystyrene/p-hydroxystyrene/p-tert-butoxycarbonyloxystyrene), poly(p-

1-cyclohexyloxyethoxystyrene/p-hydroxystyrene/p-tetrahydropyranyloxystyrene), poly(p-tert-butoxystyrene/p-hydroxystyrene), poly(p-tert-butoxycarbonyloxystyrene/p-hydroxystyrene), poly(p-tetrahydropyranyloxystyrene/p-hydroxystyrene), poly(p-hydroxystyrene/styrene/tert-butylacrylate), poly(p-hydroxystyrene/styrene/tert-amylacrylate), poly(p-hydroxystyrene/styrene/1-methylcyclohexylacrylate), poly(p-hydroxystyrene/mevalonolactoneacrylate), poly(p-hydroxystyrene/styrene/2-methyl-2-adamanthylacrylate), poly(p-1-octyloxyethoxystyrene/p-hydroxystyrene/p-acetyloxystyrene), poly(p-1-benzyloxyethoxystyrene/p-hydroxystyrene/p-acetyloxystyrene), poly[p-1-(3-cyclobenzylpropyl)oxyethoxy/p-hydroxystyrene/p-tert-butoxycarbonyloxystyrene] and poly(p-1-ethoxyethoxystyrene/p-hydroxystyrene/p-acetyloxystyrene).

These polymers may be used alone or in combination of two or more thereof.

Weight-average molecular weight (Mw) of the polymer shown by the general formula [11] is generally 3,000 to 50,000, preferably 5,000 to 25,000, more preferably 5,000 to 20,000.

Molecular weight dispersion (Mw/Mn) of the polymer shown by the general formula [11] is generally 1.0 to 3.5, preferably 1.0 to 2.5, more preferably 1.0 to 1.5.

The polymer (or the resin) soluble in an alkaline developing solution is, for example, one shown by the following general formula [12]:

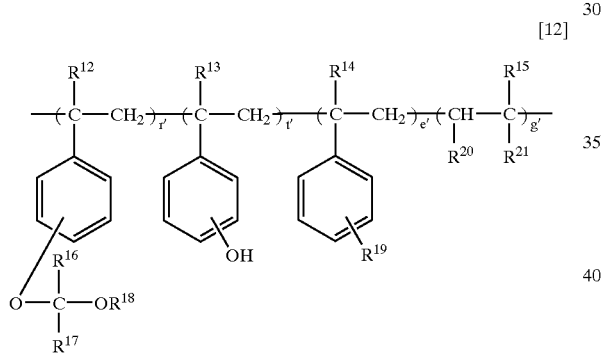

[12]

(wherein, r', e' and g' are 0 or a natural number and t' is a natural number, providing that $0 \leq r'/r'+t'+e'+g' \leq 0.2$, $0 \leq e'/r'+t'+e'+g' \leq 0.2$, $0 \leq g'/r'+t'+e'+g' \leq 0.2$ and $0 \leq r'+e'+g'/r'+t'+e'+g' \leq 0.2$, $R^{12}$, $R^{13}$, $R^{14}$, $R^{15}$, $R^{16}$, $R^{17}$, $R^{18}$, $R^{19}$, $R°$ and $R^{21}$ are the same as defined above.)

Specific examples of the polymer shown by the general formula [12] include, for example, poly(p-hydroxystyrene), poly(p-1-ethoxyethoxystyrene/p-hydroxystyrene), poly(p-1-ethoxyethoxystyrene/p-hydroxystyrene/p-tert-butoxystyrene), poly(p-1-ethoxyethoxystyrene/p-hydroxystyrene/p-tert-butoxycarbonyloxystyrene), poly(p-1-ethoxypropoxystyrene/p-hydroxystyrene), poly(p-1-isobutoxyethoxystyrene/p-hydroxystyrene), poly(p-1-cyclohexyloxyethoxy styrene/p-hydroxystyrene), poly(p-tert-butoxystyrene/p-hydroxystyrene), poly(p-tert-butoxycarbonyloxystyrene/p-hydroxystyrene), poly(p-tetrahydropyranyl oxystyrene/p-hydroxystyrene), poly(p-hydroxystyrene/styrene/tert-butylacrylate), poly(p-hydroxystyrene/styrene/tert-amylacrylate), etc.

Ratio of p-hydroxystyrene unit in the above copolymers is 80 or more mole % relative to the whole units.

Weight-average molecular weight (Mw) of the polymer shown by the general formula [12], used in a positive type 3 components chemically amplified resist is generally 3,000 to 50,000, preferably 5,000 to 25,000, more preferably 5,000 to 20,000, and its dispersion (Mw/Mn) is generally 1.0 to 3.5, preferably 1.0 to 2.5, more preferably 1.0 to 1.5.

Weight-average molecular weight (Mw) of the polymer, shown by the general formula [12], used in a negative type 3 components chemically amplified resists is generally 1,000 to 30,000, preferably 1,500 to 10,000, more preferably 2,000 to 5,000 and its dispersion (Mw/Mn) is generally 1.0 to 2.5, more preferably 1.0 to 1.5.

The dissolving-inhibiting agent having pending protecting groups to become soluble in an alkaline developing solution by an action of an acid includes those shown by the following formula [13], [14] or [15]:

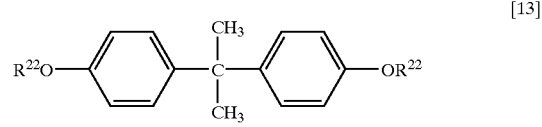

[13]

(wherein, $R^{22}$ is an acid labile group.)

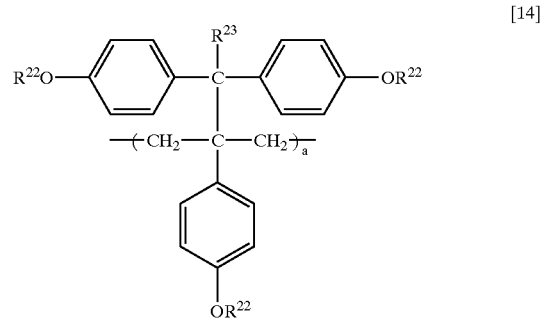

[14]

(wherein, $R^{23}$ is a hydrogen atom or a methyl group, a is a natural number and $R^{22}$ is the same as defined above.)

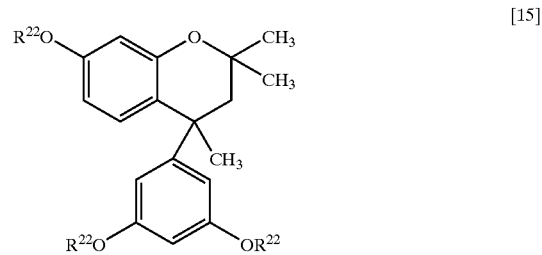

[15]

(wherein, $R^{22}$ is the same as defined above.)

The acid labile group shown by $R^{22}$ in the general formulae [13], [14] and [15] includes, for example, a tert-butoxycarbonyl group, a tert-amyloxycarbonyl group, a tetrahydropyranyl group, a tert-butyl group, a tert-amyl group, a 1-ethoxyethyl group, a 1-ethylpropyl group, a 1-cyclohexyloxyethyl group, a 1-isobutyloxyethyl group, etc.

Specific examples of the dissolving inhibiting agent shown by the general formula [13] include, for example, 2,2-bis(p-tert-butoxyphenyl)propane, 2,2-bis(p-tert-butoxycarbonyloxyphenyl)propane, 2,2-bis(p-tetrahydropyranyl oxyphenyl)propane, 2,2-bis(p-1-ethoxyethoxyphenyl)propane, 2,2-bis (p-1-cyclohexyloxyphenyl)propane, 2,2-bis(p-1-isobutoxyethoxyphenyl)propane, etc.

Specific examples of the dissolving inhibiting agent shown by the general formula [14] include, for example, tris(p-tert-butoxyphenyl)methane, tris(p-tert-butoxycarbonyloxyphenyl)methane, tris(p-tetrahydropyranyloxyphenyl)methane, tris(p-1-ethoxyethoxyphenyl)methane, tris(p-1-cyclohexyloxyphenyl)methane, tris(p-1-isobutoxyethoxyphenyl)methane, 1,1,1-tris (p-tert-butoxyphenyl)ethane, 1,1,1-tris(p-tert-butoxycarbonyloxyphenyl)ethane, 1,1,1-tris(p-tetrahydropyranyloxyphenyl)ethane, 1,1,1-tris(p-1-ethoxyethoxyphenyl) ethane, 1,1,1-tris(p-1-cyclohexyloxyphenyl)ethane, 1,1,1-tris(p-1-isobutoxyethoxyphenyl)ethane, 2,2,3-tris(p-tert-butoxyphenyl)-2-methylbutane, 2,2,3-tris(p-tert-butoxycarbonyloxyphenyl)-2-methylbutane, 2,2,3-tris(p-tetrahydropyranyloxyphenyl)-2-methylbutane, 2,2,3-tris(p-1-ethoxyethoxyphenyl)-2-methylbutane, 2,2,3-tris(p-1-cyclohexyloxyphenyl)-2-methylbutane, 2,2,3-tris(p-1-isobutoxyethoxyphenyl)-2-methylbutane, etc.

Specific examples of the dissolving inhibiting agent shown by the general formula [15] include, for example, 3,4-dihydro-4-(2,4-di-tert-butoxyphenyl)-7-(tert-butoxy)-2,2,4-trimethyl-2H-1-benzopyrane, 3,4-dihydro-4-(2,4-di-tert-butoxycarbonyloxyphenyl)-7-(tert-butoxycarbonyloxy)-2,2,4-trimethyl-2H-1-benzopyrane, 3,4-dihydro-4-(2,4-di-tetrahydropyranyloxyphenyl)-7-(tetrahydropyranyloxy)-2,2,4-trimethyl-2H-1-benzopyrane, 3,4-dihydro-4-[2,4-di-(1-ethoxyethoxy)phenyl]-7-(1-ethoxyethoxy)-2,2,4-trimethyl-2H-1-benzopyrane, 3,4-dihydro-4-[2,4-di-(1-cyclohexyloxy)phenyl]-7-(1-cyclohexyloxy)-2,2,4-trimethyl-2H-1-benzopyrane, 3,4-dihydro-4-[2,4-di-(1-isobutoxyethoxy)phenyl]-7-(1-isobutoxyethoxy)-2,2,4-trimethyl-2H-1-benzopyrane, etc.

An amount of the dissolving inhibiting agent shown by the general formulae [13], [14] and/or [15] to be used in a positive type 3 components chemically amplified resists is generally 5 to 30 wt %, preferably 15 to 25 wt % relative to a weight of total polymer.

The cross-linking agent which cross-links polymers to make it soluble in an alkaline developing solution by heat treatment in the presence of an acid includes one shown by the following general formula [16] or [17]:

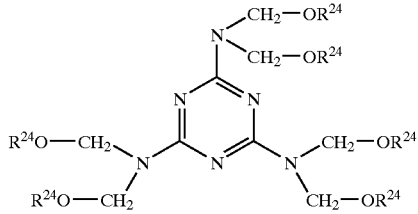

[16]

(wherein, $R^{24}$ is each independently a hydrogen atom or a lower alkyl group.)

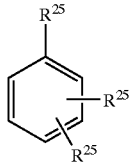

[17]

(wherein, $R^{25}$ is each independently a hydrogen atom or a lower alkoxymethyl group.)

The lower alkyl group shown by $R^{24}$ in the general formula [16] may be straight chained, branched or cyclic and includes one having generally 1 to 6 carbon atoms, which is specifically exemplified by a methyl group, an ethyl group, an n-propyl group, an isopropyl group, a cyclopropyl group, an n-butyl group, an isobutyl, a sec-butyl group, a tert-butyl group, a n-pentyl group, an isopentyl group, a sec-pentyl group, a tert-pentyl group, a neopentyl group, a cyclopentyl group, an n-hexyl group, an isohexyl group, a sec-hexyl group, a tert-hexyl group, a 1-methylpentyl group, a 2-methylpentyl group, a cyclohexyl group, etc.

The alkoxy group in the lower alkoxymethyl group shown by $R^{25}$ in general formula [17] may be straight chained, branched or cyclic and includes one having generally 1 to 6 carbon atoms, which is specifically exemplified by a methoxy group, an ethoxy group, an n-propoxy group, an isopropoxy group, a cyclopropoxy group, an n-butoxy group, an isobutoxy group, a tert-butoxy group, a sec-butoxy group, an n-pentyloxy group, an isopentyloxy group, a cyclopentyloxy group, an n-hexyloxy group, an isohexyloxy group, a cyclohexyloxy group, an 1-methylpentyloxy group, etc.

Specific examples of the cross-linking agent shown by the general formula [16] include 2,4,6-tris[1,3,5-bis(methoxymethyl)amino]-1,3,5-triazine, 2,4,6-tris[1,3,5-bis(ethoxymethyl)amino]-1,3,5-triazine, 2,4,6-tris[1,3,5-bis(isopropoxymethyl)amino]-1,3,5-triazine, 2,4,6-tris[1,3,5-bis(tert-butoxy)amino]-1,3,5-triazine, 2,4,6-tris[1,3,5-bis(cyclohexyloxymethyl)amino]-1,3,5-triazine, 2,4,6-tris(methoxymethylhydroxymethyl)amino-1,3,5-triazine, 2,4-bis[bis(methoxymethyl)amino]-6-methoxymethylhydroxymethylamino-1,3,5-triazine, etc.

Specific examples of the crosslinking agent shown by the general formula [17] include 1,2,3-tris(methoxymethyl)benzene, 1,2,3-tris(ethoxymethyl) benzene, 1,2,3-tris(isopropoxymethyl)benzene, 1,2,3-tris(tert-butoxy)benzene, 1,2,3-tris(cyclohexyloxymethyl)benzene, 1,2,4-tris(methoxymethyl)benzene, 1,2,4-tris(ethoxymethyl)benzene, 1,2,4-tris(isopropoxymethyl)benzene, 1,2,4-tris(tert-butoxy)benzene, 1,2,4-tris(cyclohexyloxymethyl)benzene, 1,3,5-tris(methoxymethyl)benzene, 1,3,5-tris(ethoxymethyl)benzene, 1,3,5-tris(isopropoxymethyl)benzene, 1,3,5-tris(tert-butoxy)benzene, 1,3,5-tris(cyclohexyloxymethyl)benzene, 1,2-bis(methoxymethyl)benzene, 1,2-bis(isopropoxymethyl)benzene, 1,2-bis(cyclohexyloxymethyl)benzene, 1,3-bis(methoxymethyl)benzene, 1,3-bis(isopropoxymethyl)benzene, 1,3-bis(cyclohexyloxymethyl)benzene, 1,4-bis(methoxymethyl)benzene, 1,4-bis(isopropoxymethyl)benzene, 1,4-bis(cyclohexyloxymethyl)benzene, etc.

An amount of the cross-linking agent shown by the general formula [16] and/or [17] to be used in a negative type chemically amplified resist is generally 5 to 30 wt %, preferably 15 to 25 wt % relative to the total amount of the polymer.

The optionally used basic compound includes, for example, pyridine, picoline, triethylamine, tri-n-butylamine, tri-n-octylamine, dioctylmethylamine, dicyclohexylmethylamine, N-methylpyrrolidine, N-methylpiperidine, triethanolamine, triisopropanolamine, dimethyldodecylamine, dimethylhexadecylamine, tribenzylamine, tris[2-(2-methoxyethoxy)ethyl]amine, tetramethylammonium hydroxide, tetraethylammonium hydroxide, tetra-n-butylammonium hydroxide, polyvinylpyridine, poly(vinylpyridine/methyl methacrylate), etc. They may be used alone or in combination of two or more thereof.

The optionally used acidic compound includes those such as phthalic acid, succinic acid, malonic acid, salicylic acid, o-acetylbenzoic acid, o-nitrobenzoic acid, thiosalicylic acid, diphenolic acid, succinimide, saccharin, ascorbic acid, etc.

The optionally used ultra violet ray absorber includes, for example, 9-diazofluorenone, 1-diazo-2-tetralone, 9-diazo-10-phenanthrone, 2,2',4,4'-tetrahydroxybenzophenone, 9-(2-methoxyethoxy)methylanthracene, 9-(2-ethoxyethoxy)methylanthracene, 9-(4-methoxybutoxy)methylanthracene, (9-anthracene methylacetate, dihydroxyflavanone, quercetin, trihydroxyflavanone, 4,4'-dihydroxybenzophenone, etc.

The optionally used surfactant includes, for example, fluorine-containing nonionic surfactants such as Fluorad (trade name of a product of Sumitomo 3M, Ltd.), Surflon (trade name of a product of Asahi Glass Co., Ltd.), Unidyne (trade name of a product of Daikin Ind. Ltd.), Megafac (trade name of a product of Dainippon Ink & Chemicals, Inc.) and Eftop (trade name of a product of Tohkem Products Corp.), polyethylene glycol, polypropylene glycol, polyoxyethylene cetyl ether, etc.

An amount of the optionally used basic compound, acidic compound, ultra violet ray absorber and/or surfactant is generally 0.000001 to 1 wt %, preferably 0.00001 to 0.5 wt % relative to the total amount of the polymer in any kind of resist.

The solvent includes, for example, methyl cellosolve acetate, ethyl cellosolve acetate, propylene glycol monomethyl ether, propylene glycol monomethyl ether acetate, propylene glycol monoethyl ether acetate, methyl lactate, ethyl lactate, propyl lactate, 2-ethoxyethyl acetate, methyl pyruvate, ethyl pyruvate, methyl 3-methoxypropionate, ethyl 3-methoxypropionate, N,N-dimethylformamide, N,N-dimethylacetamide, cyclohexanone, methylethyl ketone, 2-heptanone, β-propiolactone, β-butyrolactone, γ-butyrolactone, γ-valerolactone, δ-valerolactone, 1,4-dioxane, diethylene glycol monomethyl ether, diethylene glycol dimethyl ether, ethylene glycol monoisopropyl ether, N-methyl-2-pyrrolidone, etc. These solvents may be used alone or in combination of two or more thereof.

An amount of the solvent to be used in a chemically amplified resist is generally 3 to 10 times, preferably 3 to 7 times of a weight of total solid in any kind of resist.

Further, for the purpose of realizing an ultra-fine processing aiming at a resolution of 0.1 μm or lower by an irradiation with electron beam or $F_2$ excimer laser, a resist for surface resolution has been proposed (see, for example, JP-A-9-189998) in order to form a pattern by forming a thin membrane on an overcoat composed of novolac resin, etc, subjecting only this thin membrane to a chemically amplified reaction, and then conducting a silylation reaction and a plasma etching (dry etching), and the sulfonium salt of the present invention can be used for the resist of this type.

The resist for surface resolution is used in a state of a diluted solution, and ratios of amounts of acid generator such as the sulfonium salt of the present invention, the basic compound, the surfactant, etc. are the same as mentioned above. An amount of the solvent is, for example, generally 15 to 40 wt parts, preferably 20 to 30 wt parts relative to the total amount of the solid content.

In the positive type resist for surface resolution, the composition of a chemically amplified negative type resist mentioned above can be used as it is (in surface resolution process, a negative type resist is reversed to a positive one by silylation), and an amount of the solvent to be used is generally 15 to 40 wt parts, preferably 20 to 30 wt parts relative to the total amount of the solid content.

Also, in the negative type resist for surface resolution, the composition of a chemically amplified positive type resist mentioned above can be used as it is (in surface resolution process, a positive type resist is reversed to a negative one by silylation), and an amount of the solvent to be used is generally 15 to 40 wt parts, preferably 20 to 30 wt parts relative to the total amount of the solid content.

Roles of the sulfonium salt of the present invention, when used as an acid generator in a positive type chemically amplified resist, will be explained in detail below.

Firstly, when the sulfonium salt of the present invention is irradiated with deep ultra violet ray, excimer laser light and the like, an acid is generated according to the photoreaction as shown by the following scheme:

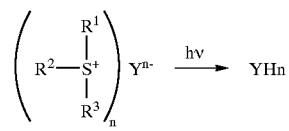

By a heat treatment after the exposure step, the protecting group of a phenolic hydroxyl group is subjected to a chemical change to convert into a phenolic hydroxyl group by an action of an acid generated from the sulfonium salt as shown in the following scheme, to become alkaline soluble and dissolve out into a developing solution in a developing process.

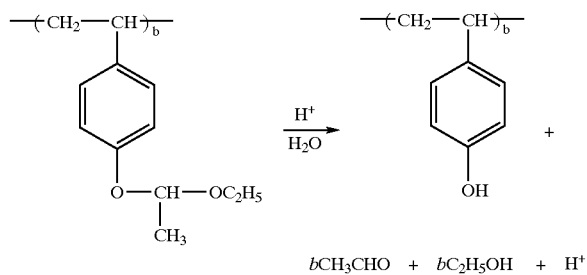

As a result, there is caused a large difference in the solubility to the alkaline developing solution between a non-exposed area where the above reaction does not occur and an exposed area, whereby a positive type pattern having a good contrast is formed. Further, since an acid to be generated is a carboxylic acid and its volatility is low, when the sulfonium salt of the present invention is used as an acid generator for a positive type chemically amplified resist, ultra-fine pattern profile and roughness of side walls can be improved.

Additionally, since a counter anion of the sulfonium salt of the present invention is a fluorine-containing carboxylic acid, it hardly be aggregated in a solution and providing an effect to prevent a generation of fine particles.

<2> Next, use of the sulfonium salt of the present invention as a cationic photopolymerization initiator will be explained.

The sulfonium salt of the present invention generates an acid by an irradiation of light. When a various kind of α, β-ethylenically unsaturated monomer is present in a reaction system with the irradiation, a polymerization rapidly proceeds.

Polymerization or copolymerization of α, β-ethylenically unsaturated monomers using the sulfonium salt of the present invention as a polymerization initiator can be performed, for example, by conducting a polymerization reaction of the sulfonium salt compound of the present invention and α, β-ethylenically unsaturated monomers in a suitable solvent or in the absence of a solvent under inert gas atmosphere if necessary, in accordance with the conventional methods.

The α, β-ethylenically unsaturated monomers include one shown by the following general formula [18]:

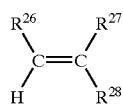

[18]

(wherein, $R^{26}$ is a hydrogen atom, a lower alkyl group, a carboxyl group, a carboxyalkyl group, an alkoxycarbonyl group, a cyano group or an aldehyde group, $R^{27}$ is a hydrogen atom, a lower alkyl group, a carboxyl group, an alkoxycarbonyl group, a cyano group or a halogen atom, $R^{28}$ is a hydrogen atom or a lower alkyl group, a haloalkyl group, an aryl group which may have substituents, an aliphatic heterocyclic group, an aromatic heterocyclic group, a halogen group, an alkoxycarbonyl group, a cyano group, a cyano-containing alkyl group, an acyloxy group, a carboxyl group, a carboxyalkyl group, an aldehyde group, a carbamoyl group or an N-alkylcarbamoyl group. $R^{26}$ and $R^{27}$ may form an aliphatic ring together with the adjacent —C=C— group.)

The lower alkyl group shown by $R^{26}$ to $R^{28}$ in the general formula [18] may be straight chained, branched or cyclic and includes one having generally 1 to 6 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a tert-pentyl group, a 1-methylpentyl group, an n-hexyl group, an isohexyl group, a cyclopropyl group, a cyclopentyl group, a cyclohexyl group, etc.

The carboxyalkyl group shown by $R^{26}$ and $R^{28}$ includes one derived by substituting a part of the hydrogen atoms of the lower alkyl groups mentioned above with a carboxyl group, which is specifically exemplified by a carboxymethyl group, a carboxyethyl group, a carboxypropyl group, a carboxybutyl group, a carboxypentyl group, a carboxyheptyl group, etc.

The alkoxycarbonyl group shown by $R^{26}$ to $R^{28}$ includes, for example, one having preferably 2 to 11 carbon atoms, and which is specifically exemplified by a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group a decyloxycarbonyl group, etc.

The halogen atom shown by $R^{27}$ and $R^{28}$ includes a fluorine atom, a chlorine atom, a bromine atom and an iodine atom.

The haloalkyl group shown by $R^{28}$ includes, for example, one having 1 to 6 carbon atoms derived by halogenating (for example, fluorinating, chlorinating, brominating, iodinating, etc.) the lower alkyl group mentioned above, which is specifically exemplified by a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, 5-chloropentyl, 6-chlorohexyl group, etc.

The aryl group in the aryl group which may have substituents shown by $R^{28}$ includes a phenyl group, a tolyl group, a xylyl group, a naphthyl group, etc., and the substituent includes a lower alkoxy group, etc. Specific examples of the substituted aryl group include a methoxyphenyl group, a tert-butoxyphenyl group, etc.

The aliphatic heterocyclic group shown by $R^{28}$ is, for example, 5-membered or 6-membered ring having preferably 1 to 3 hetero atoms as a different kind atom such as nitrogen atom, oxygen atom and a sulfur atom, and which is specifically exemplified by a pyrrolidyl-2-one group, a piperidyl group, a piperidino group, a piperazinyl group, a morpholino group, etc.

The aromatic heterocyclic group shown by $R^{28}$ is, for example, 5-membered or 6-membered ring having preferably 1 to 3 hetero atoms as a different kind atom such as nitrogen atom, oxygen and sulfur atoms, and which is specifically exemplified by a pyridyl group, an imidazolyl group, a thiazolyl group, a furanyl group and a pyranyl group.

The cyano-containing alkyl group shown by $R^{28}$ is, for example, one derived by substituting a part of the hydrogen atoms of the lower alkyl groups mentioned above with a cyano group, which is specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group, a 6-cyanohexyl group, etc.

The acyloxy group shown by $R^{28}$ includes, for example, one derived from carboxylic acid having 2 to 20 carbon atoms, and which is specifically exemplified by an acetyloxy group, a propionyloxy group, a butylyloxy group, a pentanoyloxy group, a hexanoyloxy group, a heptanoyloxy group, an octanoyloxy group, a nonanoyloxy group, a decanoyloxy group, a benzoyloxy group, etc.

The N-alkylcarbamoyl group shown by $R^{28}$ includes one derived by substituting a part of the hydrogen atoms of the alkylcarbamoyl group, which is specifically exemplified by an N-methylcarbamoyl group, an N-ethylcarbamoyl group, an N-n-propylcarbamoyl group, an N-isopropylcarbamoyl group, an N-n-butylcarbamoyl group, an N-t-butylcarbamoyl group, etc.

The case where $R^{26}$ and $R^{28}$ are bound together with the adjacent —C=C— group to form the aliphatic ring includes one where an unsaturated aliphatic ring having 5 to 10 carbon atoms is formed, and the ring may be a monocyclic ring or polycyclic rings. Specific examples of these rings include a norbornene ring, a cyclopentene ring, a cyclohexene ring, a cyclooctene ring, a cyclodecene ring, etc.

Specific examples of the α, β-ethylenically unsaturated monomer shown by the general formula [18] include ethylenically unsaturated aliphatic hydrocarbons having 2 to 20 carbon atoms such as ethylene, propylene, butylene and isobutylene, ethylenically unsaturated aromatic hydrocarbons having 8 to 20 carbon atoms such as styrene, 4-methylstyrene, 4-ethylstyrene and divinylbenzene, alkenyl esters having 3 to 20 carbon atoms such as vinyl formate, vinyl acetate, vinyl propionate and isopropenyl acetate, halogen-containing ethylenically unsaturated compounds having 2 to 20 carbon atoms such as vinyl chloride, vinylidene chloride, vinylidene fluoride and tetrafluoroethylene, ethylenically unsaturated carboxylic acids having 3 to 20 carbon atoms such as acrylic acid, methacrylic acid, itaconic acid, maleic acid, fumaric acid, crotonic acid, vinylacetic acid, allylacetic acid and vinylbenzoic acid (these acids may be salt form, for example, an alkaline metal salt such as a sodium salt and a potassium salt, an ammonium salt, etc.), ethylenically unsaturated carboxylates such as methyl methacrylate, ethyl methacrylate, propyl methacrylate, butyl methacrylate, 2-ethylhexyl methacrylate, methyl acrylate, ethyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenoate, cyano-containing ethylenically unsaturated compounds having 3 to 20 carbon atoms such as acrylonitrile, methacrylonitrile and allyl cyanide, ethylenically unsaturated amide compounds having 3 to 20 carbon atoms such as acrylamide and methacrylamide; ethylenically unsaturated aldehydes having 3 to 20 carbon atoms such as acrolein and croton aldehyde, ethylenically unsaturated aliphatic heterocyclic amines having 5 to 20 carbon atoms such as N-vinylpyrrolidone and vinylpiperidin, ethylenically unsaturated aromatic heterocyclic amines having 5 to 20 carbon atoms such as vinylpyridine and 1-vinylimidazole, etc.

These monomers may be used alone or in a suitable combination of two or more thereof.

The method of the above polymerization includes, for example, a solution polymerization, a bulk polymerization, a suspension polymerization, an emulsion polymerization, etc.

The polymerization solvent includes halogenated hydrocarbons such as chloroform, methylene chloride and 1,2-dichloroethne, hydrocarbon solvents such as toluene, benzene and xylene, N-dimethylformamide, dimethylsulfoxide, etc. These solvents may be used alone or in a suitable combination of two or more thereof.

The polymerization is desirably conducted under an inert atmosphere. The inert gas includes nitrogen gas, argon gas, etc.

The amount of the sulfonium salt compound of the present invention to be used varies also depending on the kinds of the α, β-ethylenically unsaturated monomers used, however, it is generally 0.1 to 200 wt %, preferably 1 to 50 wt % relative to the amount of the α, β-ethylenically unsaturated monomers.

The concentration of the α, β-ethylenically unsaturated monomers in polymerization varies also depending on the kinds of the α, β-ethylenically unsaturated monomers used, however, it is generally 1 to 100 wt % (non-solvent), preferably 10 to 80 wt %.

The polymerization temperature is generally −78 to 100° C., preferably −20 to 50° C.

The polymerization time varies depending on reaction conditions such as reaction temperature, the kinds of the sulfonium salt compound of the present invention and the α, β-ethylenically unsaturated monomers to be reacted and their concentrations, however, it is generally 1 to 50 hours.

The treatment after the reaction can be conducted in accordance with the conventional manner in this field of technology.

The sulfonium salt compound of the present invention is one having a counter anion being a carboxylic acid containing fluorine atoms, and therefore, it is decomposed by exposing to ultra violet ray, deep ultra violet ray, excimer laser, etc., or irradiation with electron beams, X-ray, etc., to generate a carboxylic acid containing fluorine atoms. Consequently, when this is used as an acid generator for chemically amplified resists, the generated acid is the low volatile carboxylic acids, and therefore, a profile of ultra-fine pattern or an edge roughness can be improved.

Further, the sulfonium salt compound of the present invention is also useful as a cationic photopolymerization initiator since it generates an acid by an irradiation of light.

The present invention will be further explained in detail referring to following Examples, however, these examples are not intended to limit the present invention by any means.

EXAMPLES

Example 1

Synthesis of Triphenylsulfonium Heptafluorobutanoate (Method A)

In 200 ml of benzene were dissolved 21.1 g (0.1 mol) of diphenylsulfoxide, and 42.0 g (0.2 mol) of trifluoroacetic acid anhydride were added dropwise thereto at 0 to 5° C., followed by stirring and stirred at 0 to 5° C. for 30 minutes. And then, 15.0 g (0.1 mol) of trifluoromethane sulfonic acid were added dropwise thereto at 0 to 5° C. and allowed to react with stirring at 0 to 20° C. for 3 hours. After completion of the reaction, 500 ml of n-hexane was poured into the resultant and the obtained oily substance separated by decantation was crystallized from methylene chloride/n-hexane, followed by filtration and drying, to give 37.9 g (yield: 92%) of triphenylsulfonium trifluoromethanesulfonate as a white crystal.

Melting point: 132–134° C.

$^1$HNMR (CDCl$_3$) δ ppm: 7.30–7.79 (15H, m, Ar—H).

In aqueous methanol solution were dissolved 20.6 g (50 mmol) of the resulting triphenylsulfonium trifluoromethanesulfonate, and passed through an activated strong base type anion exchange resin (Amberlite IRA-900 by Organo Corp.). To the elutant solution was added 24.8 g (60 mmol) of heptafluorobutyric acid and allowed reacting with stirring at room temperature for 1 hour. After completion of the reaction, the solvent was removed and the residue was dissolved in 200 ml methylene chloride, washed with water 3 times and concentrated under reduced pressure to give 28.4 g (yield: 84%) of triphenylsulfonium heptafluorobutanoate as a white crystal.

Melting point: 71–74° C.

$^1$HNMR (CDCl$_3$) δ ppm: 7.67–7.80 (15H, m, Ar—H).

Example 2

Synthesis of Triphenylsulfonium Pentadecafluorooctanoate (Method B)

In 600 ml of tetrahydrofuran were dissolved, 21.1 g (0.1 mol) of diphenylsulfoxide under nitrogen atmosphere, then 27.2 g (0.25 mol) of chlorotrimetylsilane was poured into them. A Grignard reagent prepared from 39.3 g (0.25 mol) of bromobenzene and 6.1 g of magnesium metal in accordance with the conventional manner was added dropwise thereto under ice-cooling, followed by allowing to react at the same temperature for 3 hours. After completion of the reaction, 500 ml of 24% aqueous solution of hydrobromic acid was added dropwise to the reaction solution at 0 to 5° C., and then 600 ml of toluene was poured into them, followed by stirring and separation, the organic layer was extracted twice with 120 ml of 12% aqueous solution of hydrobromic acid, and the resulting aqueous layers were combined and extracted 3 times with 480 ml of methylene chloride. The resulting organic layer was dried over anhydrous magnesium sulfate and concentrated under reduced pressure to give 23.3 g (yield: 68%) of triphenylsulfonium bromide as a white crystal.

Melting point: 288–290° C.

$^1$HNMR (CDCl$_3$) δ ppm: 7.72–7.82 (9H, m, Ar—H), 7.85–7.89 (6H, m, Ar—H).

In 100 ml of methylene chloride were dissolved 17.2 g (0.05 mol) of the resulting triphenylsulfonium bromide at room temperature in the shade, and 26.0 g (0.05 mol) of silver pentadecafluorooctanoate were added thereto, followed by allowing to react at room temperature overnight with stirring. After completion of the reaction, the resulting precipitate was separated by filtration and the mother liquor was concentrated under reduced pressure, followed by crystallization from ethyl acetate to give 29.1 g (yield: 86%) of triphenylsulfonium pentadecafluorooctanoate as a white crystal.

Melting point: 130–130.5° C.
$^1$HNMR (CDCl$_3$) δ ppm: 7.66–7.80 (15H, m, Ar—H).

Example 3

Synthesis of Triphenylsulfonium O-trifluoromethylbenzoate (Method C)

In 200 ml of benzene were dissolved 21.1 g (0.1 mol) of diphenylsulfoxide, and 160.0 g (0.6 mol) of aluminum bromide at room temperature were added thereto, followed by allowing to react at 80° C. for 2 hours with stirring. The reaction solution was poured into 1000 ml of ice and extracted 3 times with methylene chloride. Thus obtained organic layer was dried over anhydrous magnesium sulfate, followed by concentration under reduced pressure to give 22.0 g (yield: 64%) of triphenylsulfonium bromide as a white crystal.

Melting point: 288–290° C.
$^1$HNMR (CDCl$_3$) δ ppm: 7.72–7.82 (9H, m, Ar—H), 7.85–7.89 (6H, m, Ar—H).

In 100 ml of methylene chloride were dissolved 17.2 g (0.05 mol) of the resulting triphenylsulfonium bromide at room temperature in the shade, 26.0 g (0.05 mol) of silver o-trifluoromethyl benzoate were added thereto, and then followed by allowing to react at room temperature overnight with stirring. After completion of the reaction, the resulting precipitate was separated by filtration and the mother liquor was concentrated under reduced pressure to give 21.7 g (yield: 96%) of triphenylsulfonium o-trifluoromethylbenzoate as a white crystal.

Melting point: 91–93° C.
$^1$HNMR (CDCl$_3$) δ ppm: 7.14–7.52 (4H, m, Ar—H), 7.65–7.82 (15H, m, Ar—H).

Example 4 to 15

Using various sulfoxides and desired benzene or its derivatives, syntheses were conducted according to any of the methods described in Examples 1 to 3 to get corresponding sulfonium salts. The obtained results are shown in Table 1 and 2.

TABLE 1

| Example | Sulfoxide Derivative | Benzene Derivative | Carboxylic Acid Derivative | Method | Product | Physical Property | $^1$HNMR (CDCl$_3$) δ ppm |
|---|---|---|---|---|---|---|---|
| 4 | Diphenyl sulfoxide | Bromobenzene | m-Trifluoro methylbenzoic Acid | Example 2 | Triphenylsulfonium m-Trifluoromethyl benzoate | Pale yellowish viscous oil | 7.32 (1H, t, Ar—H), 7.48 (1H, d, Ar—H), 8.21 (1H, d, Ar—H), 8.29 (1H, s, Ar—H), 7.60–7.70 (15H, m, Ar—H) |
| 5 | Diphenyl sulfoxide | Bromobenzene | Silver p-Trifluoro methylbenzoate | Example 2 | Triphenylsulfonium p-Trifluoromethyl benzoate | Yellowish viscous oil | 7.44 (2H, d, Ar—H), 8.10 (2H, d, Ar—H), 7.61–7.74 (15H, m, Ar—H) |
| 6 | Diphenyl sulfoxide | Bromobenzene | Silver o-Fluoro benzoate | Example 2 | Triphenylsulfonium o-Fluoro benzoate | White crystal mp. 132–135° C. | 6.85 (1H, t, Ar—H), 6.97 (1H, t, Ar—H), 7.14 (1H, q, Ar—H), 7.61–7.70 (9H, m, Ar—H), 7.75 (1H, t, Ar—H), 7.80–7.87 (6H, m, Ar—H) |
| 7 | Diphenyl sulfoxide | Bromobenzene | Silver m-Fluoro benzoate | Example 2 | Triphenylsulfonium m-Fluoro benzoate | White crystal mp. 76–86° C. | 6.94 (1H, t, Ar—H), 7.20 (1H, q, Ar—H), 7.68–7.85 (17H, m, Ar—H) |
| 8 | Diphenyl sulfoxide | Bromobenzene | p-Fluoro benzoic Acid | Example 2 | Triphenylsulfonium p-Fluoro benzoate | White crystal mp. 150–152° C. | 7.44 (2H, w, Ar—H), 8.11 (2H, w, Ar—H), 7.61–7.75 (15H, m, Ar—H) |
| 9 | Diphenyl sulfoxide | Bromobenzene | Silver 2,4-Difluoro benzoate | Example 2 | Triphenylsulfonium 2,4-Difluoro benzoate | White crystal mp. 185–188° C. | 6.52–6.70 (1H, m, Ar—H), 7.68–7.87 (17H, m, Ar—H) |

TABLE 2

| Example | Sulfoxide Derivative | Benzene Derivative | Carboxylic Acid Derivative | Method | Product | Physical Property | $^1$HNMR (CDCl$_3$) δ ppm |
|---|---|---|---|---|---|---|---|
| 10 | Diphenyl sulfoxide | Bromobenzene | Silver 2,3,4,5,6-Penta Fluoro benzoate | Example 2 | Triphenylsulfonium 2,3,4,5,6-Penta fluorobenzoate | White crystal mp. 172.5–174° C. | 7.78–7.84 (15H, m, Ar—H) |
| 11 | Diphenyl sulfoxide | Bromobenzene | Silver 4-Fluoro phenylacetate | Example 2 | Triphenylsulfonium 4-Fluorophenyl acetate | White crystal mp. 116–120° C. | 3.48 (1H, s, CH$_2$), 6.78 (2H, t, Ar—H), 7.29 (2H, q, Ar—H), 7.61–7.75 (15H, m, Ar—H) |
| 12 | Diphenyl sulfoxide | Bromobenzene | Silver Perfluoro dodecanoate | Example 2 | Triphenylsulfonium Perfluoro dodecanoate | White crystal mp. 140–143° C. | 7.68–7.78 (15H, m, Ar—H) |
| 13 | Diphenyl sulfoxide | p-Bromo toluene | Silver Pentadeca fluoro octanoate | Example 2 | (4-Methylphenyl) diphenylsulfonium pentadecafluoro octanoate | Pale brownish crystal mp. 92–94° C. | 2.46 (3H, s, CH$_3$), 7.50 (2H, d, Ar—H), 7.62–7.78 (12H, m, Ar—H) |
| 14 | Di(p-methyl phenyl) sulfoxide | Benzene | Silver Pentadeca fluoro octanoate | Example 3 | Di(4-methylphenyl) phenylsulfonium Pentadecafluoro octanoate | Pale brownish crystal mp. 81–83° C. | 2.46 (6H, s, CH$_3$) 7.48 (4H, d, Ar—H) 7.62 (4H, d, Ar—H), 7.64–7.77 (5H, m, Ar—H) |

TABLE 2-continued

| 15 | Di(p-methyl phenyl) sulfoxide | p-Bromo toluene | Silver Pentadeca fluoro octanoate | Example 2 | Tri(4-methylphenyl) sulfonium Pentadecafluoro octanoate | White crystal mp. 69.5–71.5° C. | 2.45 (9H, s, CH$_3$), 7.48 (6H, d, Ar—H), 7.58 (6H, d, Ar—H) |

Example 16

Synthesis of bis(triphenylsulfonium) tetrafluorosuccinate (Method B)

In 100 ml of methylene chloride were added 17.2 g (0.05 mol) of triphenylsulfonium bromide obtained by synthesizing similarly as in Example 2 at room temperature in the shade, and 10.1 g (0.025 mol) of silver tetrafluorosuccinate were added thereto, followed by allowing to react at room temperature overnight with stirring. After completion of the reaction, the resulting precipitate was separated by filtration and the mother liquor was concentrated under reduced pressure, followed by crystallization from ethyl acetate to give 17.4 g (yield: 97%) of bis(triphenylsulfonium) tetrafluorosuccinate as a white crystal.

Melting point: 227–227.5° C. (decomposition)
$^1$HNMR (CDCl$_3$) δ ppm: 7.65–7.84 (15H, m, Ar—H).

Example 17

Synthesis of bis(triphenylsulfonium) dodecafluorosuberinate (Method B)

In 100 ml of methylene chloride were dissolved 17.2 g (0.05 mol) of triphenylsulfonium bromide, obtained by synthesizing similarly as in Example 2 at room temperature in the shade, and 15.1 g (0.025 mol) of silver dodecafluorosuberinate were added thereto, followed by allowing to react at room temperature overnight with stirring. After completion of the reaction, the resulting precipitate was separated by filtration and the mother liquor was concentrated under reduced pressure, followed by crystallization from ethyl acetate to give 21.0 g (yield: 92%) of bis(triphenylsulfonium)dodecafluorosuberinate as a white crystal.

Melting point: 140–141° C.
$^1$HNMR (CDCl$_3$) δ ppm: 7.70–7.88 (15H, m, Ar—H).

Example 18

Synthesis of bis(triphenylsulfonium) tetrafluorophthalate (Method B)

In, 100 ml of methylene chloride were dissolved 17.2 g (0.05 mol) of triphenylsulfonium bromide obtained by synthesizing similarly as in Example 2 at room temperature in the shade, and 8.60 g (0.025 mol) of silver tetrafluorophthalate were added thereto, followed by allowing to react at room temperature overnight with stirring. After completion of the reaction, the resulting precipitate was separated by filtration and the mother liquid was concentrated under reduced pressure, followed by crystallization from ethyl acetate to give 18.1 g (yield: 95%) of bis(triphenylsulfonium)tetrafluorophthalate as a pale yellow crystal.

Melting point: 75–78° C.
$^1$HNMR (CDCl$_3$) δ ppm: 7.45–7.58 (9H, m, Ar—H), 7.86 (6H, w, Ar—H).

Comparative Example 1

Synthesis of Triphenylsulfonium Octanoate

The same reaction and after treatment as in Example 2 were conducted except for using silver octanoate instead of silver pentadecafluorooctanoate in Example 2, to give triphenylsulfonyl octanoate as a colorless oily substance.

$^1$HNMR (CDCl$_3$) δ ppm: 0.84(3H, t, CH$_3$), 1.23(8H, br, CH$_2$), 1.56(2H, m, CH$_2$), 2.12(2H, t, CH$_2$), 7.65–7.74(9H, m, Ar—H), 7.86–7.90(6H, m, Ar—H).

Comparative Example 2

Synthesis of Triphenylsulfonium Benzoate

The same reaction and after treatment as in Example 2 were conducted except for using silver benzoate instead of silver pentadecafluorooctanoate in Example 2, to give triphenylsulfonyl benzoate as a white crystal.

Melting point: 136–138° C.
$^1$HNMR (CDCl$_3$) δ ppm: 7.19 (3H, m, Ar—H), 7.60–7.68 (15H, m, Ar—H), 8.07 (2H, w, Ar—H).

Comparative Example 3

Synthesis of Triphenylsulfonium Trifluoroacetate

The same reaction and after treatment as in Example 2 were conducted except for using silver trifluoroacetate instead of silver pentadecafluorooctanoate in Example 2, to give triphenylsulfonyl trifluoroacetate as a white crystal.

Melting point: 120–122° C.
$^1$HNMR (CDCl$_3$) δ ppm: 7.68–7.82 (15H, m, Ar—H).

Experimental Example 1

A chemically amplified resist composition consisting of the following ingredients was prepared:

| | |
|---|---|
| (1) Poly[4-(1-ethoxyethoxy)styrene/4-tert-butoxystyrene/ p-hydroxystyrene] [Mw: 21000, Mw/Mn: 2.00] | 6.0 g |
| (2) Bis(cyclohexylsulfonyl)diazomethane | 0.3 g |
| (3) Triphenylsulfonium heptafluorobutanoate | 0.1 g |
| (4) Organic basic compound | 0.1 g |
| (5) Surfactant | 0.1 g |
| (6) Propylene glycol monomethyl ether acetate | 45.0 g |

Experimental Examples 2 to 7

The resists were prepared similarly as in Example 1 except for using sulfonium salts listed in Table 3 below instead of triphenylsulfonium heptafluorooctanoate in the composition of Example 1 (the same amounts were used).

TABLE 3

| | |
|---|---|
| Expt. Exp. 2 | Triphenylsulfonium pentadecafluorooctanoate (Compound of Example 2) |
| Expt. Exp. 3 | Triphenylsulfonium o-trifluoromethylbenzoate (Compound of Example 3) |
| Expt. Exp. 4 | Triphenylsulfonium p-trifluorobenzoate (Compound of Example 8) |

TABLE 3-continued

| | |
|---|---|
| Expt. Exp. 5 | Triphenylsulfonium 2,4-difluorobenzoate (Compound of Example 9) |
| Expt. Exp. 6 | Triphenylsulfonium 2,3,4,5,6-pentafluorobenzoate (Compound of Example 10) |
| Expt. Exp. 7 | Triphenylsulfonium 4-fluorophenylacetate (Compound of Example 11) |

Reference Examples 1 to 4

Resists were prepared by using sulfonium salts listed in Table 4 below instead of triphenylsulfonium pentadecafluorooctanoate in the composition of Example 1 (the same amount was used).

TABLE 4

| | |
|---|---|
| Ref. Exp. 1 | Triphenylsulfonium octanoate (Compound of Comp. Exp. 1) |
| Ref. Exp. 2 | Triphenylsulfonium benzoate (Compound of Comp. Exp. 2) |
| Ref. Exp. 3 | Triphenylsulfonium trifluoroacetate (Compound of Comp. Exp. 3) |
| Ref. Exp. 4 | Triphenylsulfonium triflate |

Experimental Example 8

Using the resist compositions obtained in the above Experimental Examples 1 to 7 and Reference Examples 1 to 4, patterns were formed as follows.

Resist compositions were filtered through a 0.1 μm thick membrane filter and then spin-coated on a silicon substrate, followed by pre-baking on a hot plate at 90° C. for 90 seconds to give resist films with a thickness of 0.5 μm. To transfer patterns, the resist films were irradiated with a 248 nm KrF excimer laser stepper (NSR2005EX10B, NA=0.55, of Nikon Co. Ltd.), then baked on a hot plate at 105° C. for 90 seconds, followed by developing with a 2.38% aqueous solution of tetramethylammonium hydroxide to form resist patterns on a silicon substrate.

The resulting resist patterns were evaluated as follows, and the results are shown in Table 5. A sensitivity (Eth) was determined, and an exposure amount which resolves 0.25 μm of line-and-space at 1:1 was regarded as an optimum exposure amount, and a minimum line width of a line-and-space resolved with the optimum, was regarded as a resolution of a resist. Further, shapes of the resist patterns and roughness of patterns of 0.22 μm (edge roughness) were measured by using a scanning electron microscope.

TABLE 5

| | Sensitivity(Eop) mJ/cm$^2$ | Resolution μm | Pattern shape | Edge roughness nm |
|---|---|---|---|---|
| Expt. Exp. 1 | 45 | 0.21 | Rectangular | 10 |
| Expt. Exp. 2 | 133 | 0.21 | Rectangular | 11 |
| Expt. Exp. 3 | 84 | 0.21 | Rectangular | 15 |
| Expt. Exp. 4 | 60 | 0.21 | Rectangular | 12 |
| Expt. Exp. 5 | 44 | 0.21 | Rectangular | 11 |
| Expt. Exp. 6 | 45 | 0.21 | Rectangular | 10 |
| Expt. Exp. 7 | 46 | 0.21 | Rectangular | 12 |
| Ref. Exp. 1 | 192 | 0.22 | Slightly Taper | 56 |
| Ref. Exp. 2 | 204 | 0.22 | Slightly Taper | 52 |
| Ref. Exp. 3 | 108 | 0.25 | Poor Shape | 85 |
| Ref. Exp. 4 | 30 | 0.21 | Taper | 50 |

As obvious from the results shown in Table 5, use of sulfonium salt compounds of the present invention as an acid generator, form a pattern with higher sensitivity, higher resolution, more rectangular shape and smaller edge roughness, compared with the patterns formed by using an existing sulfonium salt having a carboxylic acid as a counter anion (which may be abbreviated as a carboxylic acid sulfonium salt hereinafter), which includes a carboxylic acid sulfonium salt having no fluorine substituents such as triphenylsulfonium octanoate and triphenylsulfonium benzoate, and a carboxylic acid sulfonium salt having less than 3 carbon atoms, although substituted with fluorine, such as triphenylsulfonium trifluoroacetate.

Further, it can be understood that same or better performances such as resolution, shape of pattern and PED are shown by using a sulfonium salt compound of the present invention than those shown by using a sulfonium salt having a sulfonic acid such as triphenylsulfonium triflate as a counter anion.

EFFECTS OF THE INVENTION

A sulfonium salt compound of the present invention is exposed by an irradiation with ultra violet ray, deep ultra violet ray, KrF excimer laser, ArF excimer laser, $F_2$ excimer laser, electron beam, X-ray or radiation, etc., and then generates an acid, that is, the sulfonium salt compound not only takes effects on improving a profile of ultra-fine patterns and edge roughness but also is useful as a cationic photopolymerization initiator.

What is claimed is:

1. A composition comprising a compound shown by the formula [1]

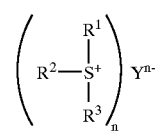

[1]

wherein $R^1$, $R^2$ and $R^3$ are each independently an aromatic hydrocarbon residual group; $Y^{n-}$ is an anion derived from a carboxylic acid having 3 or more carbon atoms with substituted fluorine atoms; n is 1 or 2; $R^1$, $R^2$ and $R^3$ being a phenyl group having substituents at o-position and/or m-position is excluded; and a diazodisulfone compound.

2. A cationic photopolymerization initiator, which comprises the the composition of claim 1.

3. An acid generator, which comprises the composition according to claim 1.

4. An acid generator for a chemically amplified resist, which comprises the composition according to claim 1.

5. A composition according to claim 1, wherein the diazodisulfone compound is shown by the formula [10]

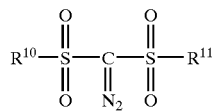

wherein, $R^{10}$ and $R^{11}$ are each independently an alkyl group.

6. A resist composition, which comprises a polymer having a pending protecting group to become soluble in an alkaline developing solution by an action of an acid and the composition according to claim 5.

7. A resist composition, which comprises a polymer soluble in an alkaline developing solution, a dissolving-inhibiting agent having a pending protecting group to become soluble in an alkaline developing solution by an action of an acid, and the composition according to claim 5.

8. A resist composition, which comprises a polymer soluble in an alkaline developing solution, a cross-linking agent to cross-link the polymer by a heat treatment in the presence of an acid to make insoluble in an alkaline developing solution, and the composition according to claim 5.

* * * * *